(12) United States Patent
Fedon et al.

(10) Patent No.: US 10,617,550 B2
(45) Date of Patent: Apr. 14, 2020

(54) KNEE BRACE HAVING A VARIABLE TENSIONING OFFSET CAM

(71) Applicant: Breg, Inc., Carlsbad, CA (US)

(72) Inventors: Shane C. Fedon, Encinitas, CA (US); Andrew M. Blecher, Encino, CA (US)

(73) Assignee: Breg, Inc., Carlsbad, CA (US)

( * ) Notice: Subject to any disclaimer, the term of this patent is extended or adjusted under 35 U.S.C. 154(b) by 722 days.

(21) Appl. No.: 14/738,774

(22) Filed: Jun. 12, 2015

(65) Prior Publication Data

US 2015/0374531 A1 Dec. 31, 2015

Related U.S. Application Data

(60) Provisional application No. 62/018,575, filed on Jun. 28, 2014.

(51) Int. Cl.
*A61F 5/01* (2006.01)
*A61F 5/02* (2006.01)

(52) U.S. Cl.
CPC .......... *A61F 5/0125* (2013.01); *A61F 5/0102* (2013.01); *A61F 5/0193* (2013.01); *A61F 5/02* (2013.01); *A61F 2005/0155* (2013.01)

(58) Field of Classification Search
CPC .... A61F 5/0102; A61F 5/0123; A61F 5/0125; A61F 5/013; A61F 5/058; A61F 5/0585; A61F 5/05841; A61F 5/05825; A61F 5/05858; A61F 2005/0134; A61F 2005/0137; A61F 2005/0144; A61F 2005/0146; A61F 2005/0148; A61F 2005/0151; A61F 2005/0153; A61F 2005/0155; A61F 2005/0165; A61F 2005/0169; A61F 2005/0179; A61F 2005/0181; A61F 5/01; A61F 5/0104; A61F 5/0106; A61F 5/0109; A61F 5/0118; A61F 2005/0132; A61F 2005/0167

See application file for complete search history.

(56) References Cited

U.S. PATENT DOCUMENTS

| | | | |
|---|---|---|---|
| 4,296,744 A | 10/1981 | Palumbo |
| 4,370,977 A | 2/1983 | Mauldin |
| 4,370,978 A | 2/1983 | Palumbo |
| 4,397,308 A | 8/1983 | Hepburn |
| 4,423,720 A | 1/1984 | Meier |
| 4,445,505 A | 5/1984 | Labour |
| 4,489,718 A | 12/1984 | Martin |
| 4,508,111 A | 4/1985 | Hepburn |

(Continued)

FOREIGN PATENT DOCUMENTS

CA 2831507 4/2015

*Primary Examiner* — Victoria J Hicks
*Assistant Examiner* — Rachel A Berezik
(74) *Attorney, Agent, or Firm* — Rodney F. Brown

(57) ABSTRACT

A knee brace to stabilize the patella has a main body positionable over the knee, a hinged longitudinal support assembly, a buttress, a buttress retention flap overlaying the buttress, a cam positioned proximal to the support assembly and a tensioning line. The buttress is positioned against the side of the knee opposite the support assembly and applies a variable compression force to the knee. The tensioning line engages the cam and operatively connects it to the buttress via the buttress retention flap to automatically vary the compression force applied to the knee in response to rotation of the support assembly.

20 Claims, 10 Drawing Sheets

(56) References Cited

U.S. PATENT DOCUMENTS

| | | | |
|---|---|---|---|
| 4,607,628 A | 8/1986 | Dashefsky | |
| 4,657,000 A | 4/1987 | Hepburn | |
| 4,733,656 A | 3/1988 | Marquette | |
| 4,805,606 A | 2/1989 | McDavid, III | |
| 5,002,045 A | 3/1991 | Spademan | |
| 5,024,216 A | 6/1991 | Shiomo | |
| 5,277,697 A | 1/1994 | France | |
| 5,383,845 A | 1/1995 | Nebolon | |
| 5,472,410 A | 12/1995 | Hamersly | |
| 5,562,605 A | 10/1996 | Taylor | |
| 5,575,764 A | 11/1996 | Van Dyne | |
| 5,599,288 A | 2/1997 | Shirley | |
| 5,613,943 A | 3/1997 | Palumbo | |
| 5,624,390 A | 4/1997 | Van Dyne | |
| 5,683,353 A | 11/1997 | Hamersly | |
| 5,759,167 A * | 6/1998 | Shields, Jr. | A61F 5/0106 602/26 |
| 5,797,864 A | 8/1998 | Taylor | |
| 5,857,988 A | 1/1999 | Shirley | |
| 5,865,776 A | 2/1999 | Springs | |
| 6,001,075 A | 12/1999 | Clemens | |
| 6,110,138 A | 8/2000 | Shirley | |
| 6,129,690 A | 10/2000 | Hamlin | |
| 6,245,034 B1 | 6/2001 | Bennett | |
| 6,287,269 B1 | 9/2001 | Osti | |
| 6,471,664 B1 | 10/2002 | Campbell | |
| 6,551,264 B1 | 4/2003 | Cawley | |
| 6,635,024 B2 | 10/2003 | Hatton | |
| 7,004,919 B2 * | 2/2006 | Gaylord | A61F 5/0109 128/882 |
| 7,059,329 B2 | 6/2006 | Mason | |
| 7,060,045 B2 | 6/2006 | Mason | |
| 7,083,586 B2 | 8/2006 | Simmons | |
| 7,189,212 B2 | 3/2007 | Popp | |
| 7,192,407 B2 | 3/2007 | Seligman | |
| 7,207,960 B2 | 4/2007 | Kenney | |
| 7,481,785 B2 | 1/2009 | Turrini | |
| 7,517,330 B2 | 4/2009 | DeHarde | |
| 7,534,217 B2 | 5/2009 | Seligman | |
| 7,811,242 B2 | 10/2010 | Seligman | |
| 7,819,830 B2 | 10/2010 | Sindel | |
| 7,846,115 B2 | 12/2010 | Seligman | |
| 7,867,183 B2 * | 1/2011 | Kazmierczak | A61F 5/0123 602/23 |
| 7,905,851 B1 | 3/2011 | Bledsoe | |
| 8,123,709 B2 | 2/2012 | DeHarde | |
| 8,376,974 B2 | 2/2013 | Nace | |
| 8,435,197 B2 | 5/2013 | Vollbrecht | |
| 8,882,688 B1 | 11/2014 | Amicec | |
| 2002/0133108 A1 | 9/2002 | Jagodzinski | |
| 2003/0144620 A1 | 7/2003 | Sieller | |
| 2011/0098618 A1 | 4/2011 | Fleming | |
| 2011/0137220 A1 * | 6/2011 | Vollbrecht | A61F 5/0125 602/16 |
| 2013/0110020 A1 * | 5/2013 | Ingimundarson | A61F 5/0123 602/16 |
| 2013/0172797 A1 * | 7/2013 | Merkley | A61F 5/0102 602/16 |
| 2013/0245523 A1 * | 9/2013 | Romo | A61F 5/0125 602/16 |
| 2014/0336554 A1 * | 11/2014 | Romo | A61F 5/0125 602/16 |
| 2015/0119777 A1 * | 4/2015 | Garrish | A61F 5/0123 602/16 |

* cited by examiner

KNEE BRACE HAVING A VARIABLE TENSIONING OFFSET CAM

This a non-provisional patent application claiming the priority of Provisional Patent Application Ser. No. 62/018,575, filed on Jun. 28, 2014, which is incorporated herein by reference.

BACKGROUND OF THE INVENTION

The present invention relates generally to orthopedic braces and, more particularly, to orthopedic knee braces.

Orthopedic braces embody a broad range of apparatuses, each having the common purpose of supporting and/or stabilizing a skeletal joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened or destabilized by injury, deformity, or other infirmity, thereby reinforcing the joint and providing a therapeutic treatment effect and/or reducing the risk of further injury while the joint is rehabilitated.

Conventional orthopedic knee braces may be generally characterized as frame braces, soft braces, or hybrid braces which include elements of both frame and soft. A frame brace typically has a relatively rigid frame which is secured to the leg of a user by one or more straps engaging the frame and circumscribing the leg. A typical configuration of the frame includes two longitudinal support assemblies which are longitudinally positioned on the opposing medial and lateral sides of the leg respectively. Each longitudinal support assembly includes a relatively rigid upper longitudinal member, a relatively rigid lower longitudinal member and a hinge rotationally connecting the longitudinal members. The hinge of the medial longitudinal support assembly is positioned adjacent to the medial side of the affected knee to be stabilized and the upper and lower longitudinal members engage the medial side of the upper and lower leg above and below the affected knee respectively. The hinge of the lateral longitudinal support assembly is similarly positioned adjacent to the lateral side of the affected knee and the upper and lower longitudinal members engage the lateral side of the upper and lower leg above and below the affected knee respectively.

The typical frame configuration also includes upper and lower cuffs which, like the longitudinal members, are relatively rigid. The upper and lower cuffs are arcuate-shaped to conform to the contours of the upper and lower legs respectively. The upper cuff is attached to and/or integral with the medial and lateral upper longitudinal members and extends orthogonally between the longitudinal members while engaging the anterior or posterior face of the upper leg. The lower cuff is correspondingly attached to and/or integral with the medial and lateral lower longitudinal members and likewise extends orthogonally between the longitudinal members while engaging the anterior or posterior face of the lower leg. In an alternate configuration of the frame, one longitudinal support assembly is omitted from the frame so that only one side of the leg, either the medial or lateral side, has a longitudinal support assembly positioned adjacent to it. Regardless of the particular frame configuration, the frame brace is designed to transfer a substantial fraction of the dynamic and static force loads on the knee to the frame, thereby supporting and stabilizing the knee.

A soft brace differs from a frame brace insofar as the soft brace lacks a frame and overall is relatively less rigid than the frame brace. The soft brace has a compression sleeve which is a tube-like structure formed from a relatively pliant and elastic material that snugly encloses the knee and segments of the upper and lower legs immediately above and below the knee respectively. The sleeve applies radial compression to the knee, thereby supporting and stabilizing the knee. The soft brace may also have one or more straps which engage the sleeve and circumscribe the leg to increase the radially-directed compressive force on the leg at the knee. The support and stabilizing function of the soft brace may be further enhanced by incorporating rigid or semi-rigid stays into the sleeve.

A hybrid brace typically combines the compression sleeve of a soft brace with the longitudinal support assemblies of a frame brace in a single brace. Like the frame brace, the longitudinal support assemblies of the hybrid brace are positioned on the medial and lateral sides of the knee respectively. However, unlike the frame brace, the longitudinal support assemblies are maintained in their desired operative positions alongside the leg by the sleeve, which typically has one or more pockets sewn into its sides to slidably receive and retain the upper and lower longitudinal members of each longitudinal support assembly. As in the case of a frame brace, an alternate configuration of the hybrid brace omits one of the longitudinal support assemblies from the brace so that only one side of the leg, either the medial or lateral side, has a longitudinal support assembly positioned adjacent to it.

Among the conditions destabilizing the knee, which can be mitigated or otherwise treated by using a knee brace, are patellar tracking disorders such as patellar subluxation and dislocation. Patellar subluxation is the undesirable side to side horizontal movement of the patella away from the central trochlear groove as the knee travels back and forth between flexion and extension. Patellar subluxation can cause chronic joint pain when the knee is statically or dynamically loaded and can ultimately lead to dislocation of the patella. Patellar subluxation is believed to be the result of many factors including anatomical irregularities of the knee and/or pelvis and/or an abnormal gait.

Knee braces, which are specifically designed to therapeutically treat patellar tracking disorders, are commonly termed patellofemoral joint tracking knee braces. Exemplary frame knee braces, which are specific to the treatment of patellar tracking disorders, are disclosed in U.S. Pat. Nos. 7,059,329; and 7,905,851. Exemplary soft knee braces, which are specific to the treatment of patellar tracking disorders, are disclosed in U.S. Pat. Nos. 5,759,167 and 7,004,919. An exemplary hybrid knee brace, which is specific to the treatment of patellar tracking disorders, is disclosed in U.S. Pat. No. 7,060,045. All of the above-recited patents are incorporated herein by reference.

Patellofemoral joint tracking knee braces typically treat patellar tracking disorders by directly engaging the side or frontal face of the patella and applying patellar retention forces directly onto the patella with the objective of maintaining the patella longitudinally centered within the trochlear groove when the knee of a user travels back and forth between flexion and extension. When patellar subluxation is in the lateral direction, which is most common, patellofemoral joint tracking knee braces engage the lateral side of the patella and apply retention forces directly onto the patella. Conversely, when patellar subluxation is in the medial direction, which is generally less common, patellofemoral joint tracking knee braces engage the medial side of the patella and apply retention forces directly onto the patella. Although the intent of the laterally or medially directed forces onto the patella is to maintain the patella centered in the trochlear groove as the knee flexes or extends, it is believed that many patellofemoral joint tracking knee braces do not achieve optimal effectiveness for their intended purpose because they impinge on the normal movement and function of the knee. As a result, many patellofemoral joint tracking knee braces do not effectively treat and stabilize knees which exhibit patellar tracking disorders.

The present invention recognizes the need for an alternate patellofemoral joint tracking knee brace which has a more effective patellar tracking disorder treatment function relative to conventional patellofemoral joint tracking knee braces known in the prior art. Accordingly, it is generally an object of the present invention to provide a patellofemoral joint tracking knee brace which satisfies the above-recited need. This object and others are accomplished in accordance with the invention described hereafter.

SUMMARY OF THE INVENTION

The present invention may be characterized as a knee brace to be worn on a knee of a user to stabilize the patella of the knee during flexion and extension of the knee. The knee brace comprises a main body, a longitudinal support assembly, a knee buttress, a buttress retention flap, a cam and a tensioning line. The main body has an anterior portion, a medial portion, a posterior portion and a lateral portion. The main body is adapted for positioning over the knee with the anterior portion adapted to cover at least in part the anterior side of the knee, the medial portion adapted to cover at least in part the medial side of the knee, the posterior portion adapted to cover at least in part the posterior side of the knee and the lateral portion adapted to cover at least in part the lateral side of the knee.

The longitudinal support assembly includes an upper longitudinal member, a lower longitudinal member, and a hinge rotatably connecting the upper longitudinal member and the lower longitudinal member. The longitudinal support assembly is positioned at the lateral or medial portion of the main body and is adapted to align with the corresponding lateral or medial side of the knee. The knee buttress is adapted for positioning against the knee and applying a variable compression force to a compression surface on the knee. A preferred knee buttress is adapted for positioning against a lateral or medial side of the knee opposite the longitudinal support assembly and applying the variable compression force to the compression surface at this same side of the knee. The buttress retention flap extends from the lateral or medial portion of the main body opposite the longitudinal support assembly and overlays the knee buttress. A preferred buttress retention flap has a first side and a second side opposite the first side and the first side is attached to and extends from the lateral or medial portion of the main body opposite the longitudinal support assembly.

The cam has an operating surface. A preferred cam is positioned at the lateral or medial portion of the main body in correspondence with the position of the longitudinal support assembly at the main body. The preferred cam may be attached to the longitudinal support assembly. The tensioning line has a first anchored end and a second anchored end and follows a tensioning line path including a first tensioning line anchor, a second tensioning line anchor and the operating surface of the cam which is positioned between the first and second tensioning line anchors. The tensioning line operatively connects the cam to the knee buttress via the buttress retention flap, thereby enabling the knee brace to automatically adjust the variable compression force applied to the compression surface in response to rotation of the upper longitudinal member and the lower longitudinal member relative to one another about the hinge.

In accordance with an embodiment of the present invention, the knee brace further comprises a buttress strap extending from the second side of the buttress retention flap and having an attachment end. The first tensioning line anchor is positioned at the lateral or medial portion of the main body in correspondence with the position of the longitudinal support assembly at the main body. The first anchored end of the tensioning line is anchored to the first tensioning line anchor and the attachment end of the buttress strap is connectable to the first tensioning line anchor.

In accordance with another embodiment of the present invention, the knee brace further comprises a buttress strap retainer positioned at the lateral or medial portion of the main body in correspondence with the position of the longitudinal support assembly at the main body. The attachment end of the buttress strap connects to the first tensioning line anchor across the buttress strap retainer.

In accordance with another embodiment of the present invention, the second tensioning line anchor is positioned more proximal to the operating surface of the cam than the first tensioning line anchor and the second anchored end of the tensioning line is anchored to the second tensioning line anchor.

In accordance with another embodiment of the present invention, the longitudinal support assembly of the knee brace is a first longitudinal support assembly, the upper longitudinal member is a first upper longitudinal member, the lower longitudinal member is a first lower longitudinal member, and the hinge is a first hinge. The knee brace further comprises a second longitudinal support assembly opposite the first longitudinal support assembly including a second upper longitudinal member, a second lower longitudinal member, and a second hinge rotatably connecting the second upper longitudinal member to the second lower longitudinal member. The first longitudinal support assembly engages the medial portion of the main body and the second longitudinal support assembly engages the lateral portion of the main body.

The present invention may be alternately characterized as a knee brace comprising a main body, a medial longitudinal support assembly, a lateral longitudinal support assembly, a knee buttress, a buttress retention flap, a tensioning line anchor, a cam and a tensioning line. The main body has an anterior portion, a medial portion, a posterior portion and a lateral portion. The main body is adapted for positioning over the knee with the anterior portion adapted to cover at least in part the anterior side of the knee, the medial portion adapted to cover at least in part the medial side of the knee, the posterior portion adapted to cover at least in part the posterior side of the knee and the lateral portion adapted to cover at least in part the lateral side of the knee.

The medial longitudinal support assembly includes a medial upper longitudinal member, a medial lower longitudinal member, and a medial hinge rotatably connecting the medial upper longitudinal member and the medial lower longitudinal member. The medial longitudinal support assembly is positioned at the medial portion of the main body and is correspondingly adapted to longitudinally align with the medial side of the knee. The lateral longitudinal support assembly includes a lateral upper longitudinal member, a lateral lower longitudinal member, and a lateral hinge rotatably connecting the lateral upper longitudinal member and the lateral lower longitudinal member. The lateral longitudinal support assembly is positioned at the lateral portion of the main body and is correspondingly adapted to longitudinally align with the lateral side of the knee.

The knee buttress is adapted for positioning against the lateral side of the knee and applying a variable compression force to a compression surface at the lateral side of the knee. The buttress retention flap overlays the knee buttress and has a first side and a second side. The first side of the buttress retention flap connects to the lateral portion of the main body and the second side of the buttress retention flap extends anteriorly away from the first side. The tensioning line anchor is positioned at the medial portion of the main body. The cam has an operating surface and the cam is likewise positioned at the medial portion of the main body;

The tensioning line has a first anchored end and a second anchored end and follows a tensioning line path including a first tensioning line anchor, a second tensioning line anchor and the operating surface of the cam positioned between the first and second tensioning line anchors. The tensioning line operatively connects the cam to the knee buttress via the buttress retention flap, thereby enabling the knee brace to automatically adjust the variable compression force applied to the compression surface in response to rotation of the medial upper longitudinal member and the medial lower longitudinal member relative to one another about the medial hinge.

The present invention may be alternately characterized as a variable tensioning assembly for a hinged orthopedic brace. The variable tensioning assembly comprises a first longitudinal member having an intersecting end, a second longitudinal member having an intersecting end, a hinge, a tensioning line, a tensioning line path, a floating anchor, an anchor, a tensioning strap and a rotatable cam. The hinge rotatably connects the intersecting end of the first longitudinal member and the intersecting end of the second longitudinal member. The tensioning line has a first anchored end and a second anchored end and the tensioning line path has corresponding first and second terminuses. The tensioning line path corresponds to a course of travel for the tensioning line between the first anchored end at the first terminus and the second anchored end at the second terminus. The tensioning line path is segmented into a vertical segment and a horizontal segment. The tensioning line has a variable travel distance within the vertical segment and a variable travel distance within the horizontal segment.

The floating anchor is at the first terminus of the tensioning line path and the first anchored end of the tensioning line is fixably anchored to the floating anchor. The anchor is at the second terminus of the tensioning line path and the second anchored end of the tensioning line is fixably anchored to the anchor at the second terminus. A preferred anchor at the second terminus has a fixed position relative to the first or second longitudinal member. The tensioning strap has a variable tension and is connected to the first anchored end at the floating anchor.

The rotatable cam is positioned in the tensioning line path. A preferred rotatable cam is attached to the intersecting end of the first or second longitudinal member. Rotation of the rotatable cam varies the travel distance in the vertical segment and the travel distance in the horizontal segment. Increasing the travel distance in the vertical segment decreases the travel distance in the horizontal segment and correspondingly increases the variable tension of the tensioning strap. Decreasing the travel distance in the vertical segment increases the travel distance in the horizontal segment and correspondingly decreases the variable tension of the tensioning strap, thereby adjusting the variable tension of the tensioning strap.

In accordance with an embodiment of the present invention, the rotatable cam has an offset point selectively positionable in response to rotation of the rotatable cam. Selective positioning of the offset point in the tensioning line path increases the travel distance in the vertical segment, decreases the travel distance in the horizontal segment and correspondingly increases the variable tension of the tensioning strap. Selective positioning of the offset point outside of the tensioning line path decreases the travel distance in the vertical segment, increases the travel distance in the horizontal segment and correspondingly decreases the variable tension of the tensioning strap.

The present invention may be alternately characterized as an orthopedic sleeve. The orthopedic sleeve has a main body and a plurality of overlays superimposed on the main body and integrally joined to the main body. Overlap areas of the overlays on the main body define enhanced compression panels. The overlap areas are interspersed with sections of the main body lacking an overlapping overlay. The sections of the main body lacking an overlapping overlay define reduced compression panels. The enhanced and reduced compression panels form an alternating pattern of different compression zones on the orthopedic sleeve.

In accordance with an embodiment of the present invention, the orthopedic sleeve is adapted to be worn on a knee of a user which has an anterior side including a patella, a posterior side including a popliteal, a medial side, and a lateral side. The main body of the sleeve has an anterior portion, a medial portion, a posterior portion and a lateral portion. The main body is adapted for positioning over the knee with the anterior portion adapted to cover at least in part the anterior side of the knee, the medial portion adapted to cover at least in part the medial side of the knee, the posterior portion adapted to cover at least in part the posterior side of the knee and the lateral portion adapted to cover at least in part the lateral side of the knee;

The plurality of overlays includes a posterior upper overlay on an upper part of the posterior portion defining a posterior upper enhanced compression panel to engage the posterior side of the knee above the popliteal, a posterior lower overlay on a lower part of the posterior portion defining a posterior lower enhanced compression panel to engage the posterior side of the knee below the popliteal, a lateral longitudinal overlay on the lateral portion defining a lateral longitudinal enhanced compression panel to engage the lateral side of the knee and a medial longitudinal overlay on the medial portion defining a medial longitudinal enhanced compression panel to engage the medial side of the knee. At least a part of the anterior portion is free of an overlay, thereby defining an anterior reduced compression panel on the at least a part of the anterior portion free of an overlay to engage the patella on the anterior side of the knee. An intermediate part of the posterior portion between the upper and lower parts of the posterior portion is free of an overlay, thereby defining a posterior intermediate reduced compression panel on the intermediate part of the posterior portion to engage the popliteal on the posterior side of the knee.

The present invention will be further understood from the drawings and the following detailed description.

BRIEF DESCRIPTION OF THE DRAWINGS

The below-listed drawing figures illustrate one or more embodiments of the present invention by way of example and not by way of limitation. Common reference characters may be used among the different drawing figures to indicate the same or similar structural elements.

Figure 8:
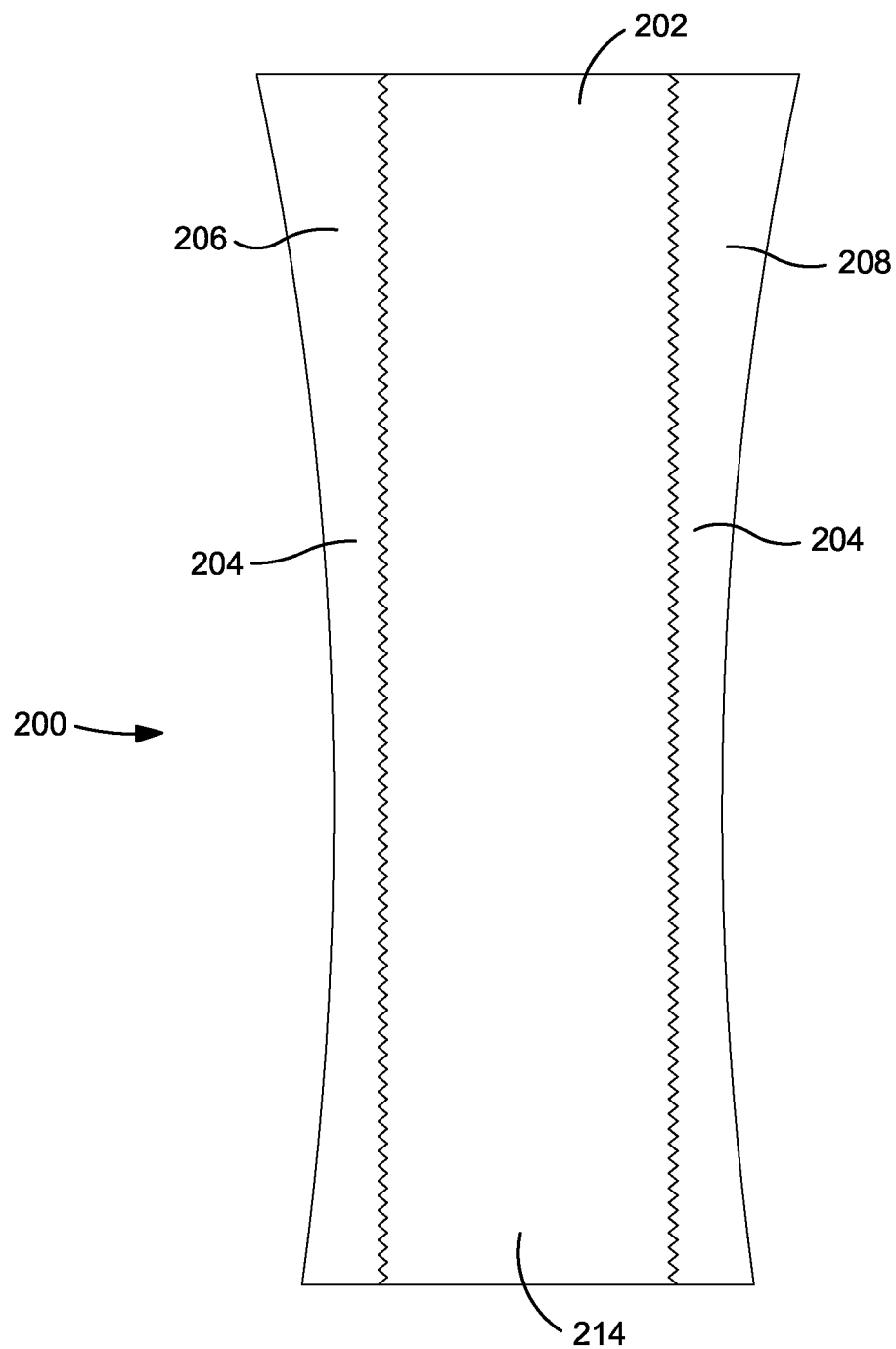
FIG. 8 is an anterior elevational view of an embodiment of a knee sleeve having utility in the knee brace of FIG. 1 or having utility as a standalone knee brace.
Figure 10:
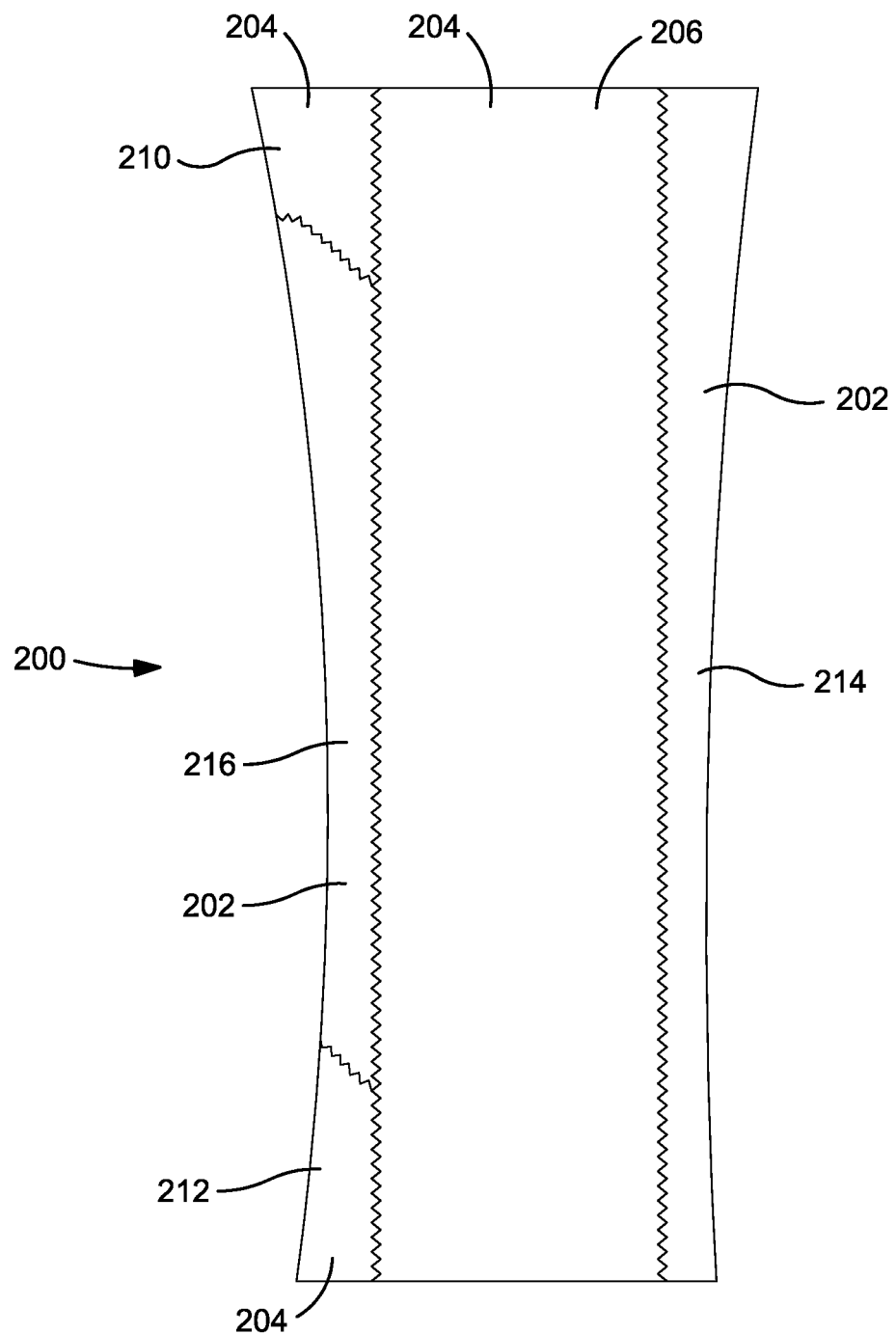
FIG. 10 is a lateral elevational view of the knee sleeve of FIG. 8.
Figure 1:
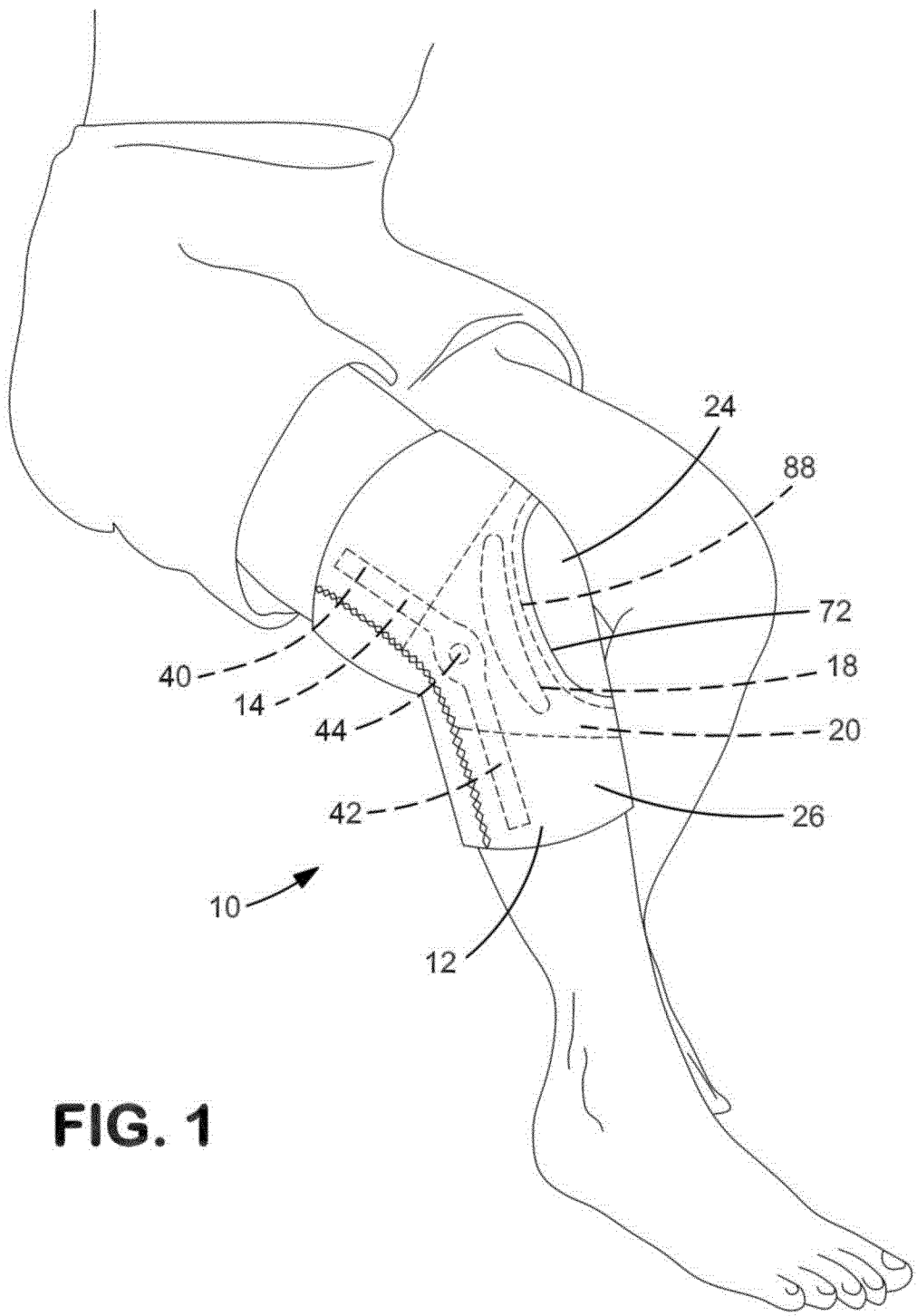
Figure 2:
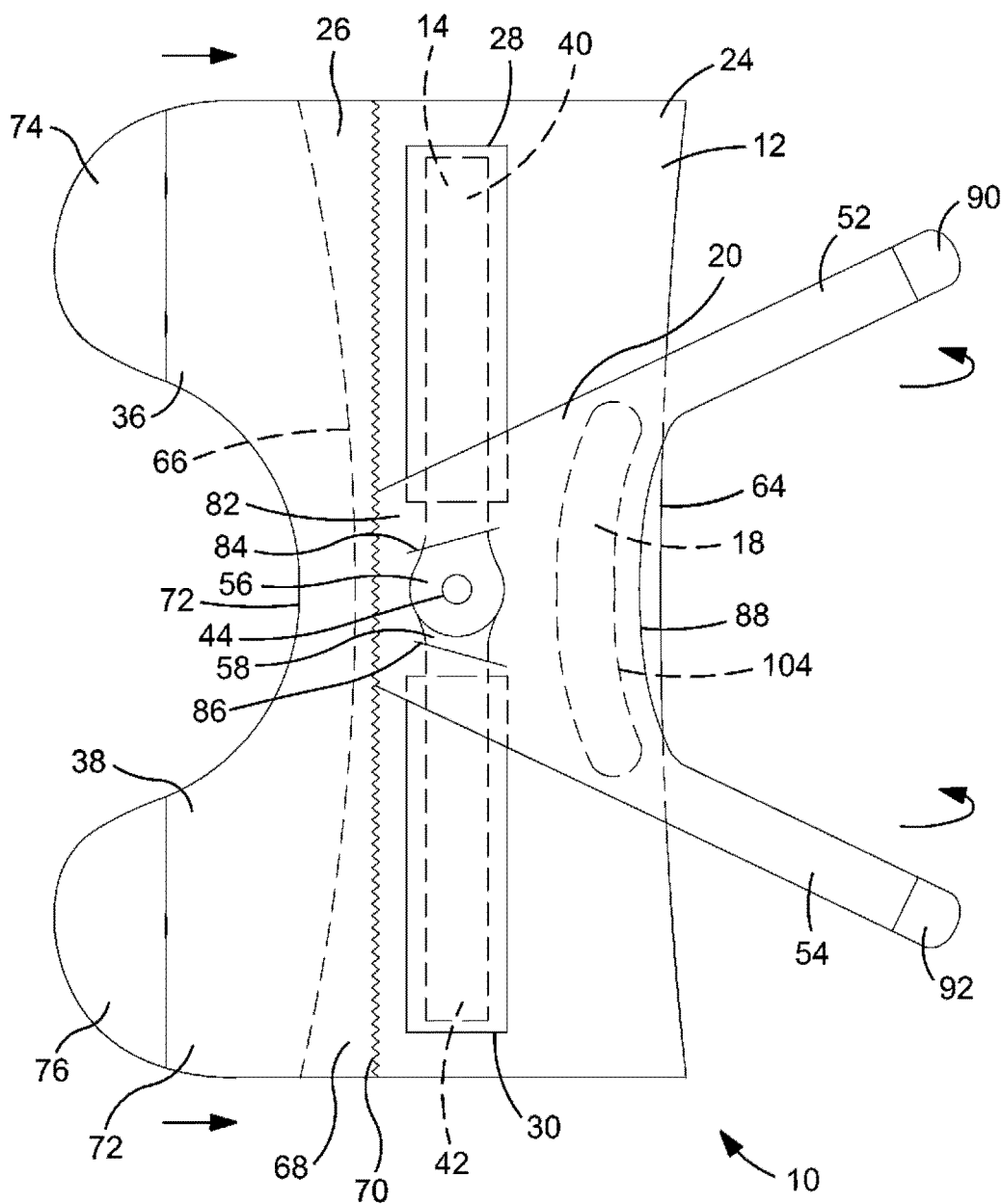
Figure 3:
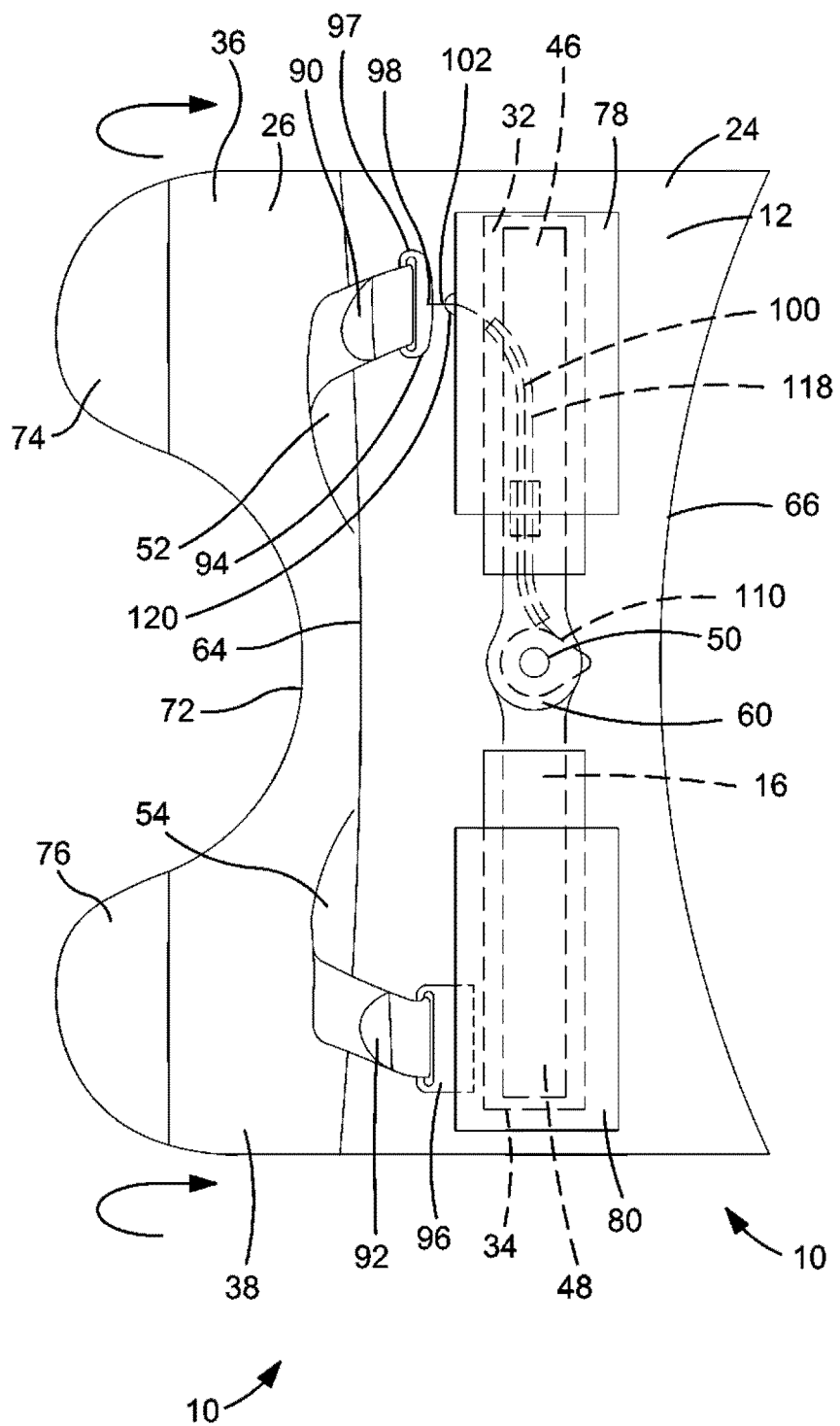
Figure 4:
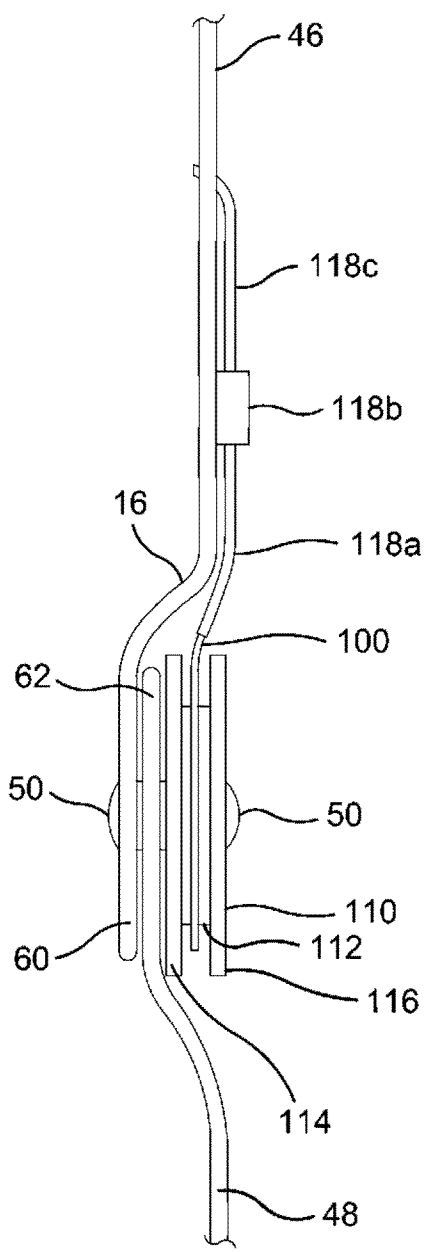
Figure 5:
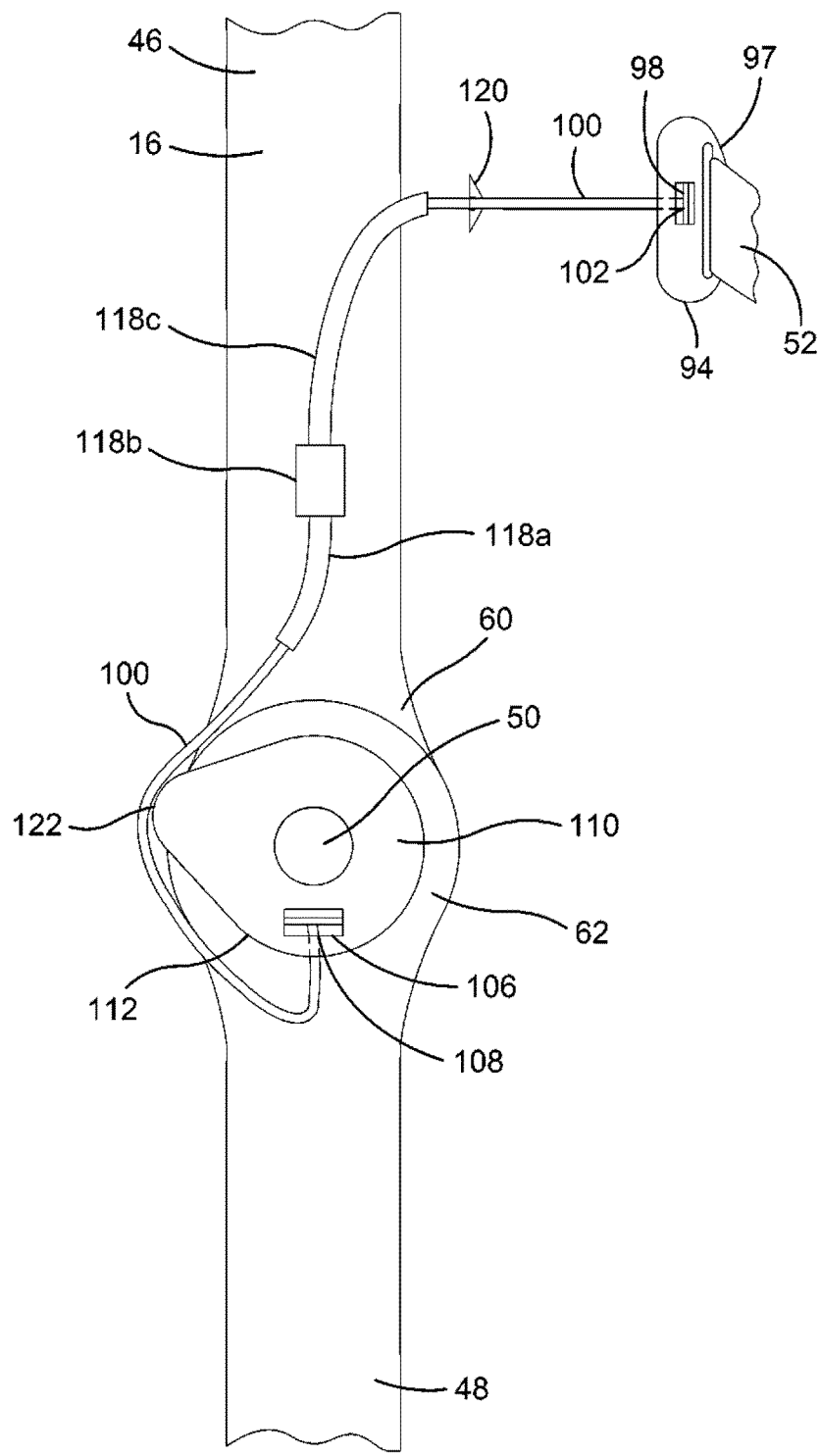
Figure 6:
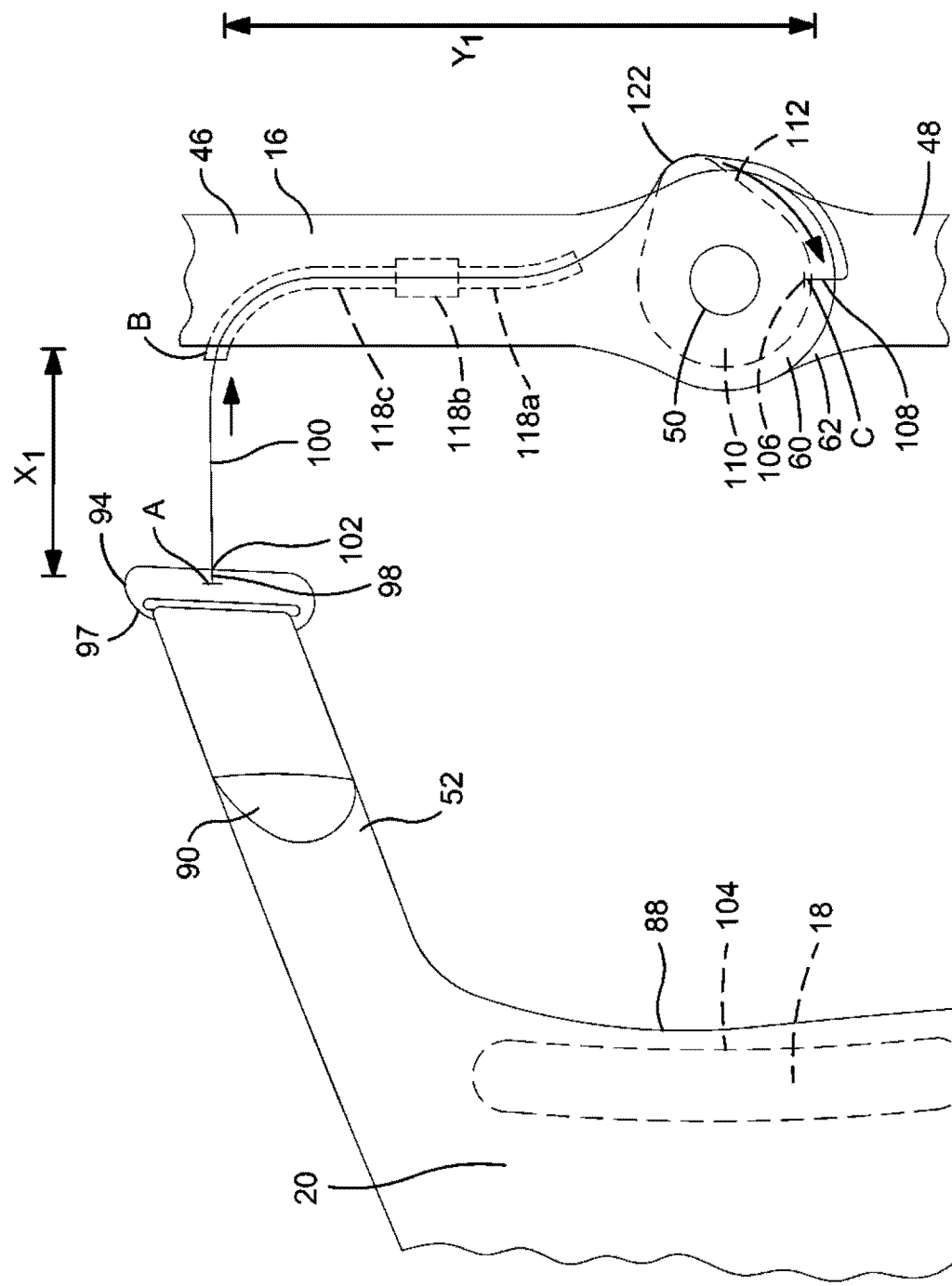
Figure 7:
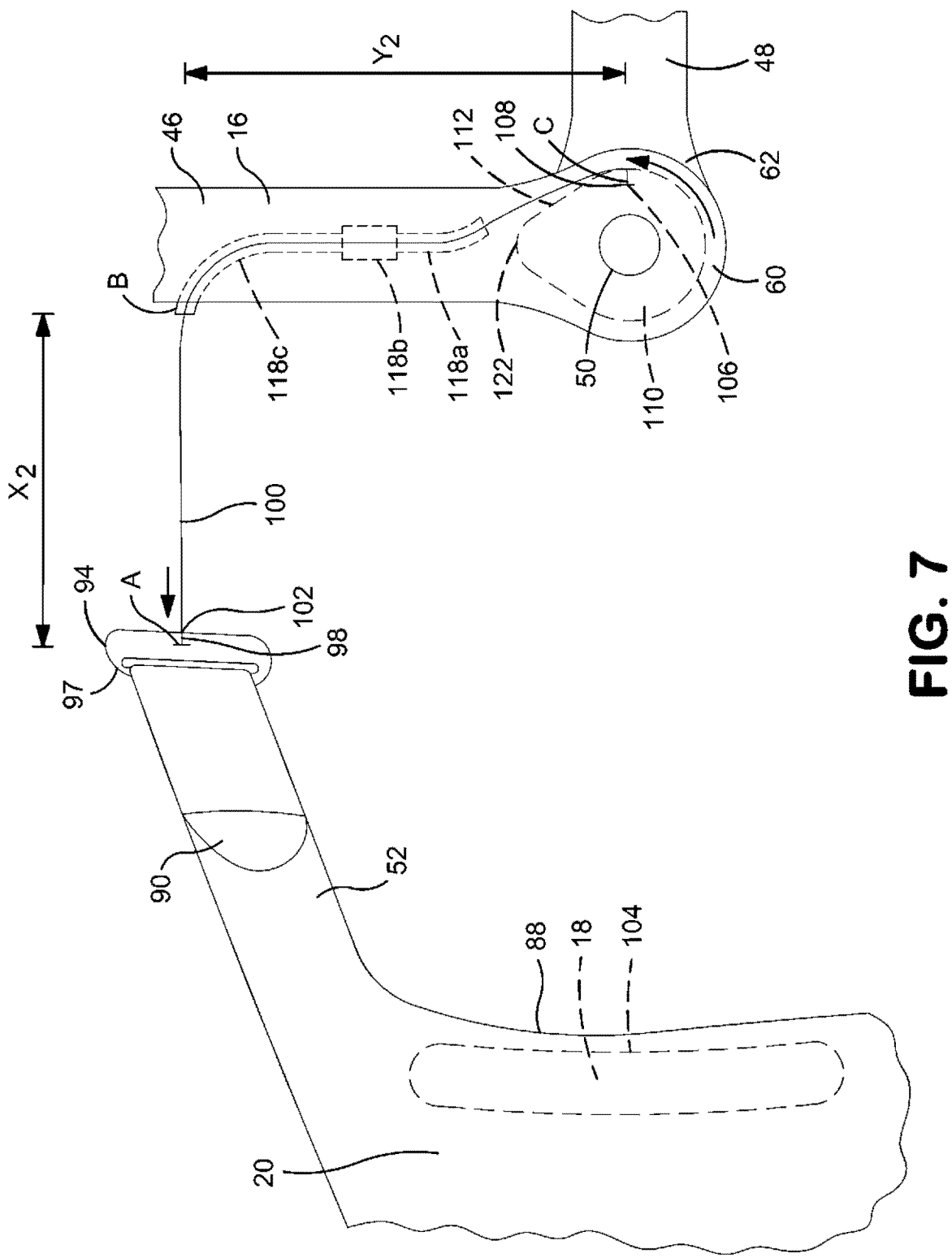
Figure 8:
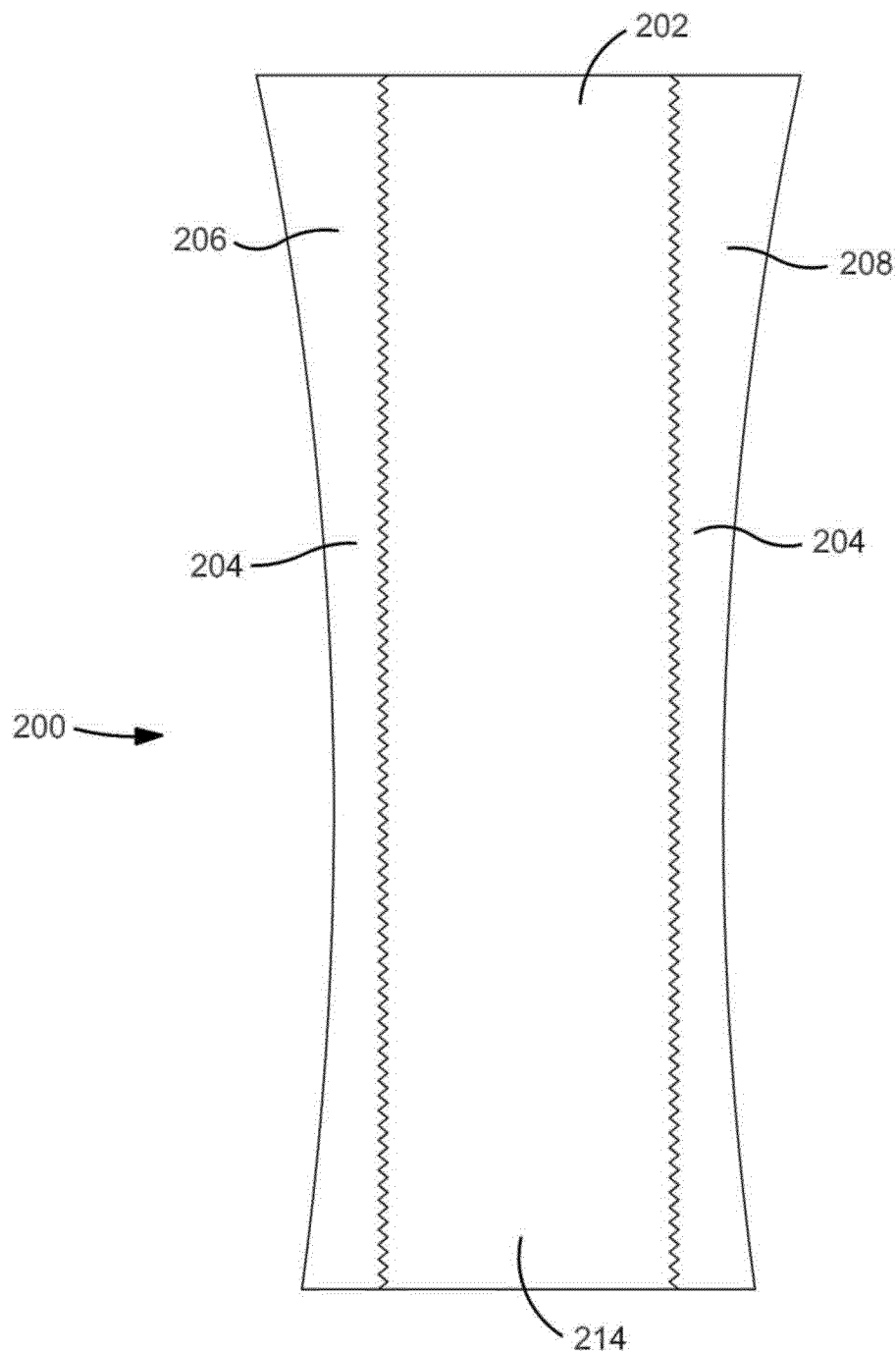
Figure 9:
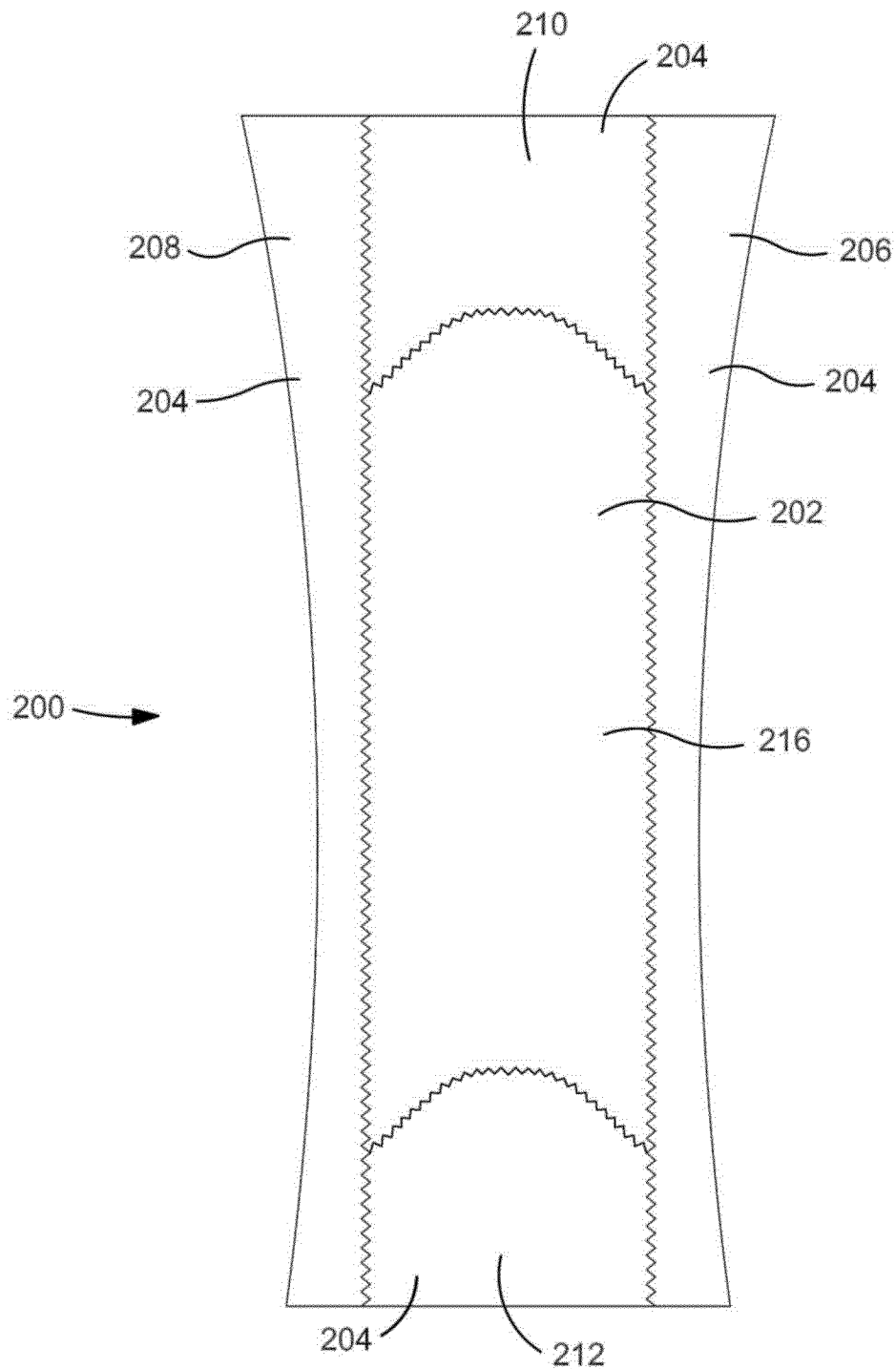
Figure 10:
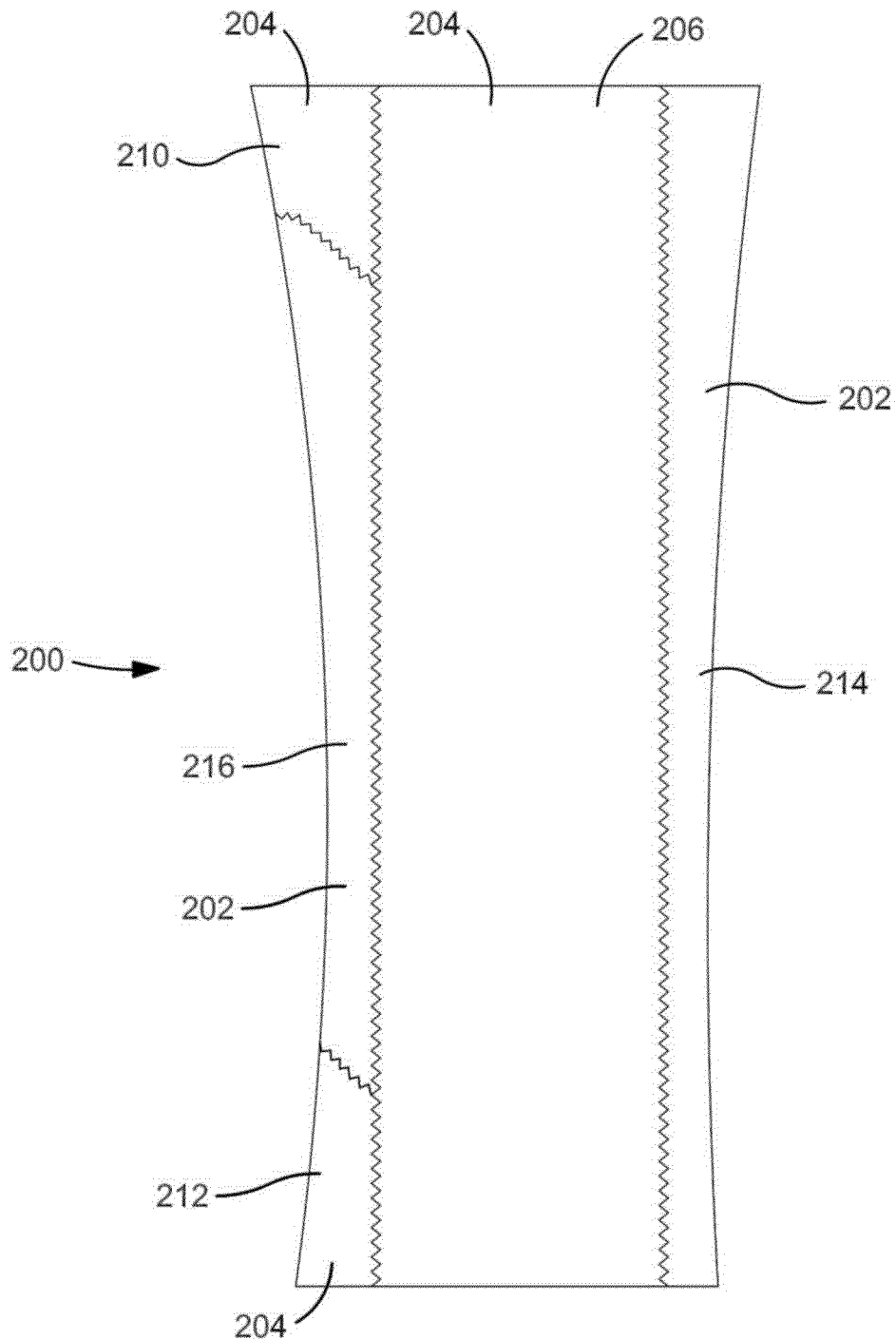

A medial elevational view of the knee sleeve of FIG. 8 of the present embodiment of the knee sleeve is not provided, but the medial elevational view simply reverses the view of FIG. 10 and is substantially identical to the view of FIG. 10 in all other respects.

DETAILED DESCRIPTION OF THE INVENTION

Figure 1:
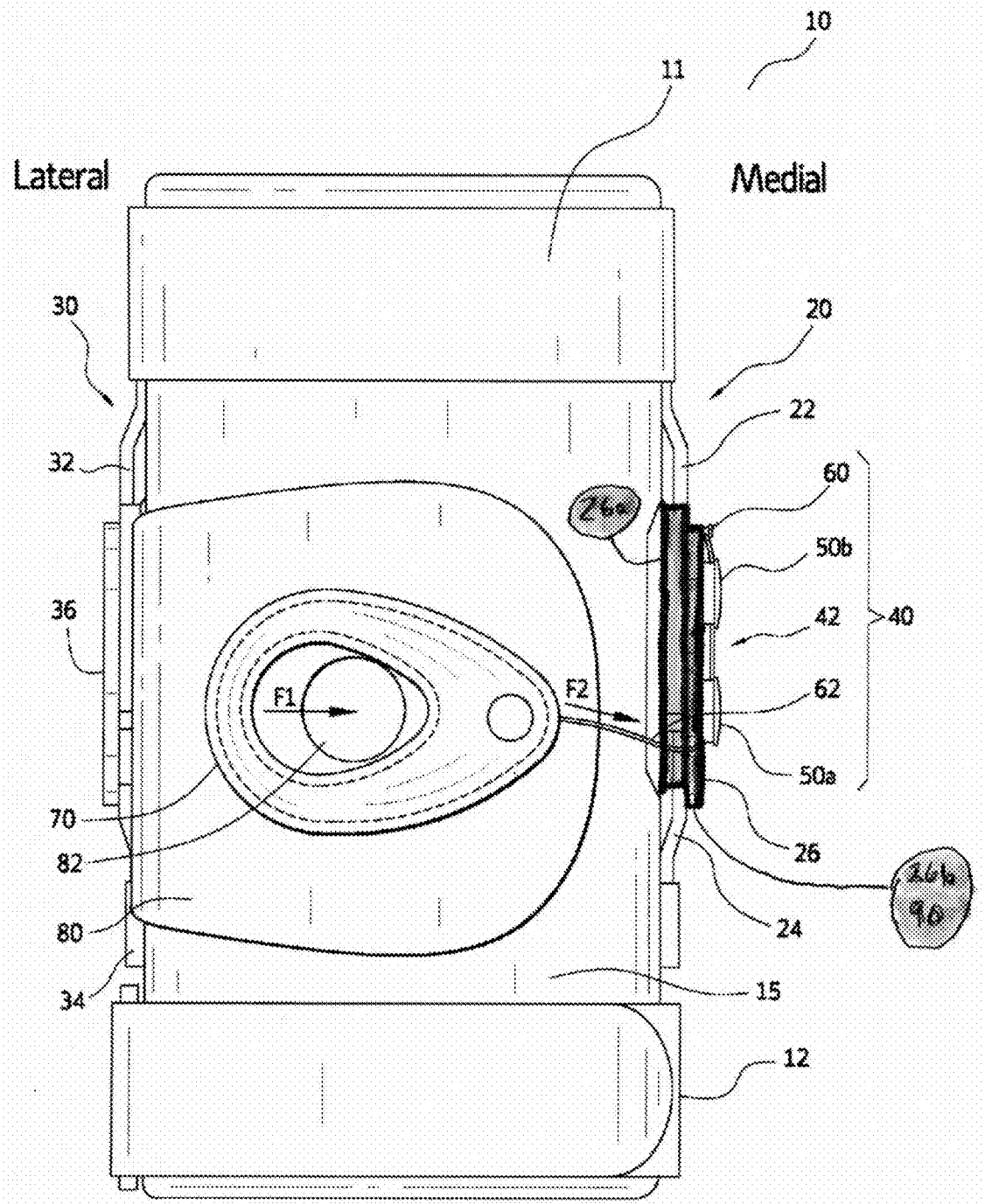
FIG. 1 is a lateral perspective view of an embodiment of a knee brace of the present invention in an operative position worn on the leg of a user.

Referring to initially FIG. 1, an embodiment of a knee brace of the present invention is shown worn on the leg of a user and is generally designated 10. The term "user" is employed herein with reference to a wearer of the knee brace 10. However, it is understood that the term "user" may also be inclusive of health care workers who assist the wearer in mounting the knee brace 10 on the wearer's leg or otherwise assist the wearer in benefiting from the advantageous functions of the knee brace 10. The relative positional terms: upper and lower, lateral and medial, distal and proximal, and anterior and posterior, are generally used herein, unless stated or implied otherwise, to describe the positioning of various elements of the knee brace 10 relative to one another and/or relative to the longitudinal or latitudinal axes of a leg or knee in its usual orientation, on which the knee brace 10 is operatively mounted. The relative positional terms, inner or inside and outer or outside, are specifically used herein, unless stated or implied otherwise, to describe the positioning of various elements of the knee brace 10 relative to the longitudinal axis of the leg in its usual orientation, on which the knee brace 10 is operatively mounted.

The knee brace 10 preferably has a patellofemoral joint tracking function which is described in detail below. The knee brace 10 is generally termed a hybrid brace because the knee brace 10 combines elements of both frame braces and soft braces. In particular, the knee brace 10 comprises a knee sleeve 12 generally of the type employed in soft braces, but specifically adapted in accordance with the teaching herein to have specific utility in the knee brace 10. The knee brace 10 further comprises a lateral longitudinal support assembly 14 and a medial longitudinal support assembly 16 (shown in FIG. 3), which are generally of the type employed in frame braces, but are specifically adapted in accordance with the teaching herein to have specific utility in the knee brace 10. The knee brace further comprises a buttress 18 which has been specifically adapted in accordance with the teaching herein to have specific utility in the knee brace 10.

For purposes of illustration, the embodiment of the knee brace 10 shown in the drawings and described herein is configured to be worn on the right leg of a user with the buttress 18 laterally positionable to resist lateral displacement of the patella on the anterior side of the right knee. However, it is apparent to one of ordinary skill in the art from the teaching herein that the knee brace 10 can be readily adapted so that the buttress is medially positionable relative to the right knee to resist medial displacement of the patella on the right knee. It is also apparent from the teaching herein that the knee brace 10 can be readily adapted for wearing on the left leg of a user with the buttress laterally or medially positionable relative to the left knee to resist lateral or medial displacement respectively of the patella on the left knee.

When the knee brace 10 is operatively mounted on a user's leg, the knee sleeve 12 is adapted to be positioned over the affected knee being stabilized and over segments of the upper and lower leg adjacent to the knee. The knee sleeve 12 comprises a main body 24, a buttress retention flap 20 and a sleeve tensioning flap 26. The main body 24 is an essentially continuous, substantially smooth, tube-like structure which is substantially free of any openings except for top and bottom openings which receive the user's foot and leg therethrough and enable the user to slide the knee sleeve 12 up over the knee during operative mounting of the knee brace 10 on the leg. The main body 24, is characterized as having an anterior portion, a medial portion, a posterior portion and a lateral portion each of which is adapted to cover, at least in part, a corresponding side of the knee. In particular, the inside face of the anterior portion is adapted to engage and cover, at least in part, the anterior side of the knee, the inside face of the medial portion is adapted to engage and cover, at least in part, the medial side of the knee, the inside face of the posterior portion is adapted to engage and cover, at least in part, the posterior side of the knee and the inside face of the lateral portion is adapted to engage and cover, at least in part, the lateral side of the knee. The anterior, medial, posterior and lateral portions of the main body 24 are all interconnected and essentially continuous with one another to substantially enclose the knee in its entirety and to also substantially enclose the adjacent segments of the upper and lower leg when the knee brace 10 is worn by a user.

The knee sleeve 12, and more specifically the main body 24, preferably lacks a patellar opening in its anterior portion which would otherwise expose the patella. Accordingly, the knee sleeve 12, and more specifically the main body 24, fully covers and encloses the patella on the anterior side of the knee as shown in FIG. 1. When the buttress retention flap 20 and sleeve tensioning flap 26 are in their operative positions with the knee brace 10 operatively mounted on the leg, both flaps 20, 26 originate at the lateral portion of the main body 24 and wrap counter-clockwise therefrom around the lateral, anterior and medial portions of the main body 24 before terminating at the medial portion of the main body 24. However, unlike the main body 24, the buttress retention flap 20 and/or the sleeve tensioning flap 26 preferably overlap and cover at most only a peripheral portion of the patella. More preferably, neither flap 20, 26 overlaps and covers any portion of the patella at all.

Figure 2:
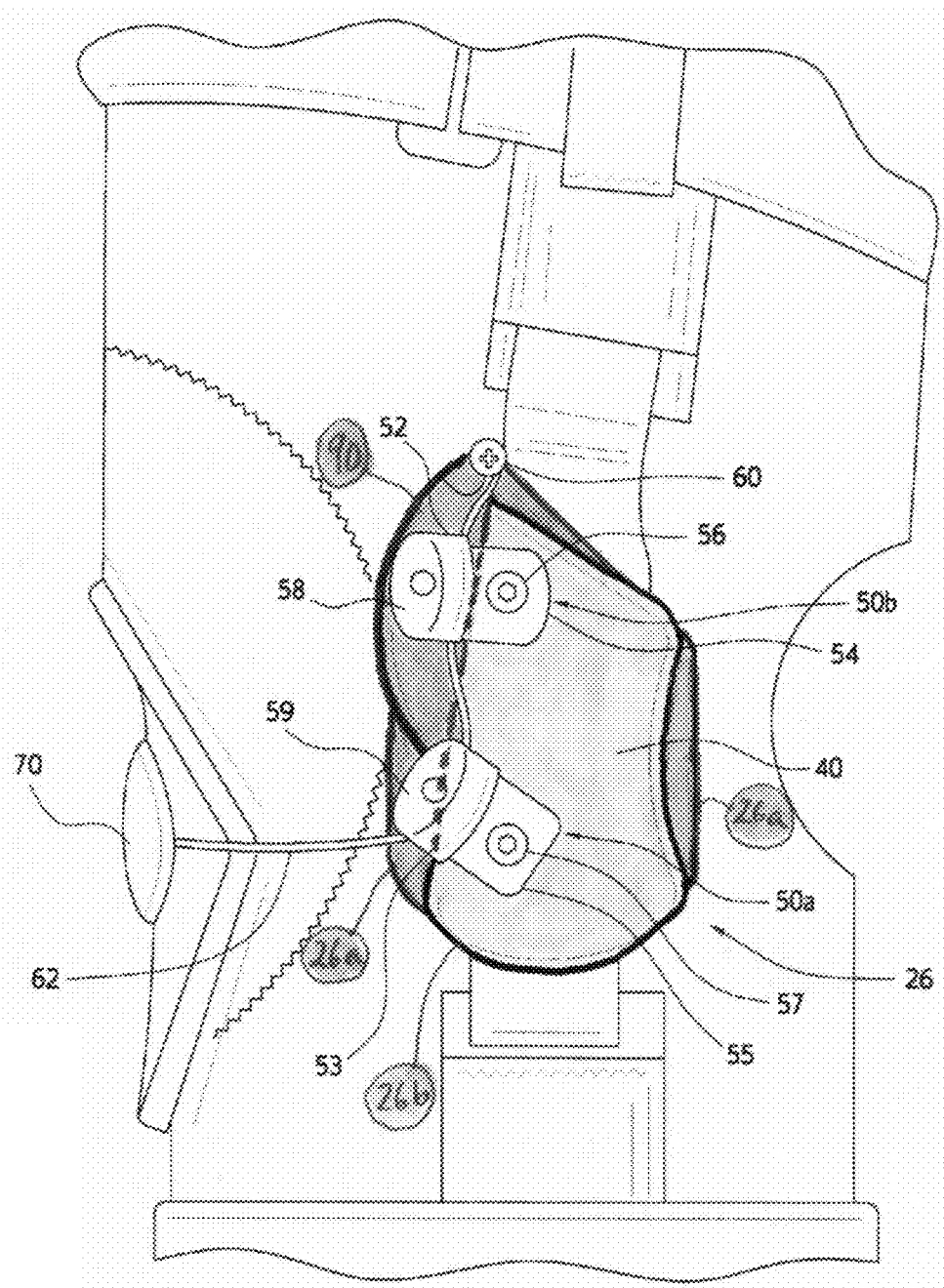
FIG. 2 is a lateral elevational view of the knee brace of FIG. 1 in an inoperative position off the leg.
Figure 3:
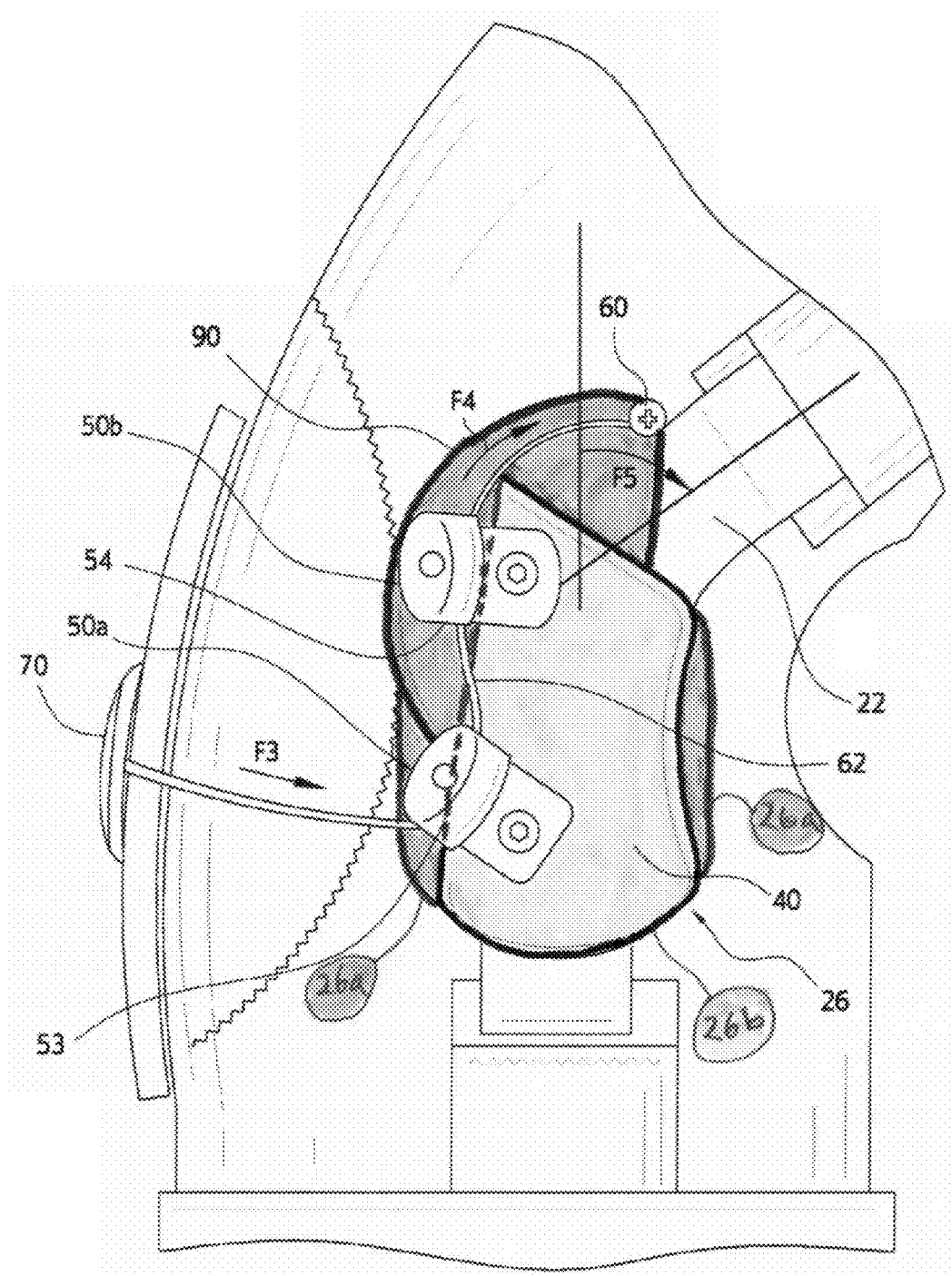
FIG. 3 is a medial elevational view of the knee brace of FIG. 1 in an inoperative position off the leg.

Further details of the knee brace 10 are described hereafter with reference to FIGS. 2 and 3 which show the knee brace 10 off the leg in a flattened inoperative position. In the lateral view of FIG. 2, the buttress retention flap 20 is laid out flat in an inoperative position by anteriorly extending it across the outside face of the lateral portion of the main body 24 to show the entire outside face of the buttress retention flap 20. The sleeve tensioning flap 26 is likewise laid out flat in an inoperative position by posteriorly extending it across the outside face of the lateral portion of the main body 24 to show the entire inside face of the sleeve tensioning flap 26. In the medial view of FIG. 3, the buttress retention flap 20 is wrapped around the lateral, anterior and medial portions of the main body 24 simulating the operative position of the flap 20. The sleeve tensioning flap 26 is laid out flat in an inoperative position with its inside face exposed as in FIG. 2, but the sleeve tensioning flap 26 is extended anteriorly across the outside face of the lateral portion of the main body 24 rather than posteriorly as in FIG. 2. Elements of the knee brace 10 which are obscured by other overlying elements are shown in phantom in FIGS. 2 and 3.

With continuing reference to FIGS. 2 and 3, the main body 24 of the knee sleeve 12 has lateral upper and lower pockets 28, 30 (omitted from FIG. 1 for clarity) and medial upper and lower pockets 32, 34 longitudinally formed thereon. The sleeve tensioning flap 26 of the knee sleeve 12 has upper and lower sleeve flap tabs 36 and 38 extending outwardly. The lateral longitudinal support assembly 14 has a lateral upper longitudinal member 40 and a lateral lower longitudinal member 42 which are rotationally connected to one another by a lateral hinge 44. The medial longitudinal support assembly 16 similarly has a medial upper longitudinal member 46 and a medial lower longitudinal member 48 which are rotationally connected to one another by a medial hinge 50. The buttress retention flap 20 has upper and lower buttress straps 52 and 54 likewise extending outwardly.

The main body 24, which is the tube portion of the knee sleeve 12, is preferably constructed as a unitary structure from a sheet of pliant material, wherein two opposing sides of the sheet are joined together in either a substantially permanent manner, e.g., by sewing, or in a selectively releasable manner, e.g., by hook-and-loop fasteners available under the trade name VELCRO. The pliant material of the main body 24 is preferably sufficiently elastically stretchable to apply a beneficial compression force to the leg when the main body 24 snugly encloses the leg. A pliant material for constructing the main body 24 satisfying the above criteria is preferably selected from among fabrics, cloths, foams, meshes, elastomers and combinations thereof. A most preferred material from among this group is an elastically stretchable synthetic cloth such as nylon or the like. Alternatively, though less preferred, the material of the main body 24 can be pliant, but substantially non-stretchable.

The lateral and medial longitudinal support assemblies 14, 16 are not limited to any one construction or configuration. Any number of longitudinal support assemblies well known in the prior art have utility as the lateral or longitudinal support assembly 14, 16 in the knee brace 10. Nevertheless, a preferred lateral longitudinal support assembly 14 is generally characterized as comprising the above-recited lateral upper longitudinal member 40, lateral lower longitudinal member 42 and rotationally interconnected lateral hinge 44. The lateral upper and lower longitudinal members 40, 42 are preferably formed from a rigid or semi-rigid material.

A semi-rigid material is defined herein as a material which exhibits a non-trivial degree of elastic deformation when subjected to the usual forces encountered by a knee brace during daily activity, but which is substantially less pliant and more rigid than the pliant material of the knee sleeve 12. In contrast, a rigid material is defined herein as a material which is more rigid than a semi-rigid material and which exhibits at most only an insignificant degree of elastic deformation when subjected to usual knee brace forces. A material for constructing the lateral upper and lower longitudinal members 40, 42 satisfying these criteria is preferably selected from among metals, plastics, composites (e.g., fiberglass, carbon fiber and the like), and combinations thereof. A most preferred material from among this group is a semi-rigid plastic.

The lateral hinge 44 is substantially any structure that rotatably connects intersecting ends 56, 58 of the lateral upper and lower longitudinal members 40, 42 respectively to one another and permits free rotation of the lateral upper and lower longitudinal members 40, 42 relative to one another. A preferred lateral hinge 44 lacks conventional adjustable rotation limits and is freely rotatable through 360° of rotation, although rotation of the hinge 44 is nevertheless subject to the physiological rotation limits of the knee itself. A preferred lateral hinge 44 substantially permanently rotatably fastens the intersecting ends 56, 58 of the lateral upper and lower longitudinal members 40, 42 respectively together at their centers, thereby functioning as a central pivot about which the lateral upper and lower longitudinal members 40, 42 are freely rotatable relative to one another. A structure satisfying these criteria is preferably a cylindrical pin having a solid configuration or a hollowed-out tubular configuration. An exemplary pin having suitability as the lateral hinge 44 may be selected from among the following hardware: rivets, grommets, bushings, bolts and complementary nuts, combinations thereof, and the like.

Figure 4:
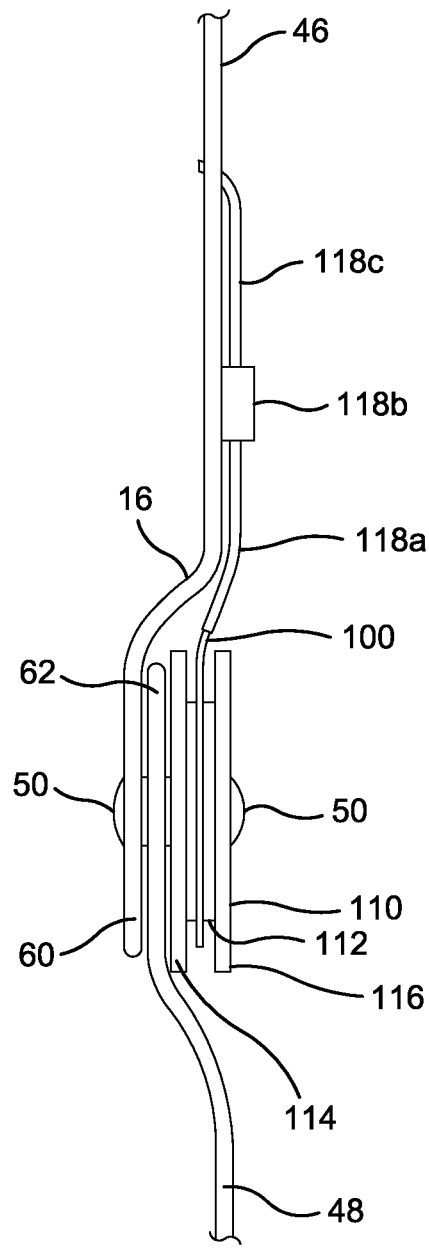
FIG. 4 is a posterior side elevational view of a variable tensioning cam and part of an associated medial longitudinal support assembly which have utility in the knee brace of FIG. 1.

The lateral upper and lower longitudinal members 40, 42 have a relatively straight configuration, but are preferably bowed slightly outward at their intersecting ends 56, 58 so that the lateral hinge 44 clears the lateral side of the knee when the knee brace 10 is mounted on a user's leg (the similarly configured medial hinge 50 is shown in FIG. 4). It is further within the scope of the present invention to enclose the lateral hinge 44 in a cushioned cover (not shown) which shields the lateral side of the knee from the lateral hinge 44, but does not impair operation of the lateral hinge 44.

The medial longitudinal support assembly 16 shown in detail in FIG. 4 preferably has the same or similar construction and configuration as the lateral longitudinal support assembly 14 described above. As such, the medial longitudinal support assembly 16 is similarly generally characterized as comprising the above-recited medial upper longitudinal member 46, medial lower longitudinal member 48 and medial hinge 50. A preferred medial hinge 50 preferably similarly permanently rotatably connects the intersecting ends 60, 62 of the medial upper and lower longitudinal members 46, 48 respectively together by rotatably fastening them at their centers, thereby functioning as a central pivot about which the medial upper and lower longitudinal members 46, 48 are freely rotatable relative to one another.

The operative position of the lateral longitudinal support assembly 14 relative to the main body 24 of the knee sleeve 12 is maintained by the lateral upper and lower pockets 28, 30 in cooperation with the lateral upper and lower longitudinal members 40, 42. Each lateral upper and lower pocket 28, 30 is preferably constructed by attaching the two opposing longitudinal sides of a strip of material, such as a pliant cloth or the like, to the outside face of the lateral portion of the main body 24 along its lateral longitudinal axis using attachment means such as sewing, while maintaining the lower end of the lateral upper pocket 28 and the upper end of the lateral lower pocket 30 open. The open lower end of the lateral upper pocket 28 receives the free end of the lateral upper longitudinal member 40 which is opposite the intersecting end 56. The open upper end of the lateral lower pocket 30 likewise receives the free end of the lateral lower longitudinal member 42 which is opposite the intersecting end 58. As a result, the lateral upper and lower longitudinal members 40, 42 are retained in engagement with the main body 24 along substantially the length of its lateral longitudinal axis when the knee brace 10 is operatively mounted on a user's leg.

The operative position of the medial longitudinal support assembly 16 relative to the main body 24 of the knee sleeve 12 is similarly maintained by the medial upper and lower pockets 32, 34 in cooperation with the medial upper and lower longitudinal members 46, 48. As such, the medial upper and lower pockets 32, 34 align with medial longitudinal axis of the main body 24. The open lower end of the medial upper pocket 32 receives the free end of the medial upper longitudinal member 46 which is opposite the intersecting end 60. The open upper end of the medial lower pocket 34 likewise receives the free end of the medial lower longitudinal member 48 which is opposite the intersecting end 62. As a result, the medial upper and lower longitudinal support members 46, 48 are retained in engagement with the main body 24 along substantially the length of its medial longitudinal axis when the knee brace 10 is operatively mounted on a user's leg.

When the knee sleeve 12 is spread out flat in an inoperative position as shown in FIGS. 2 and 3, the main body 24 has an approximately rectangular configuration with opposing top and bottom edges, which are substantially horizontal, and opposing anterior and posterior edges 64, 66, which are substantially vertical although a slight curvature is preferably permitted in the anterior and posterior vertical edges 64, 66. This slight curvature enables the main body 24 to more readily conform to the contours of the user's underlying leg including the knee when the knee brace 10 is mounted on the leg.

The sleeve tensioning flap 26, which includes the upper and lower sleeve flap tabs 36, 38, is preferably a shaped sheet of pliant material attached to and extending from the lateral portion of the main body 24 of the knee sleeve 12. In particular, the sleeve tensioning flap 26 has a first side 68 which is attached to the outside face of the lateral portion of the main body 24 along a lateral joint 70. The first side 68 of the sleeve tensioning flap 26 is alternately termed a lateral side or a pivot side because the sleeve tensioning flap 26 is freely rotatable about the pivot side 68 and lateral joint 70 when the sleeve tensioning flap 26 is in the inoperative position.

The lateral joint 70 is preferably linear and parallel to the lateral longitudinal axis of the main body 24 as shown in FIG. 2. The lateral joint 70 is also preferably proximal to the lateral longitudinal axis of the main body 24 and more preferably proximal and immediately posterior to the lateral longitudinal axis. Although not shown, it is alternatively within the scope of the present invention to attach the sleeve tensioning flap 26 to the outside face of the lateral portion of the main body 24 along an alternate longitudinal joint, such as directly along the lateral longitudinal axis of the main body 24, or along a joint parallel and proximal, but anterior, to the lateral longitudinal axis of the main body 24, or along a joint parallel and more posterior to the lateral longitudinal axis of the main body 24.

Attaching the lateral or pivot side 68 of the sleeve tensioning flap 26 to the outside face of the lateral portion of the main body 24 is effected in either a substantially permanent manner (e.g., by sewing) or in a selectively releasable manner (e.g., by hook-and-loop fasteners). Attachment is preferably effected by sewing the edge of the pivot side 68 to the outside face of the lateral portion of the main body 24 along the lateral joint 70 (or an alternate joint as described above) to form a seam. The pliant material for constructing the sleeve tensioning flap 26 is preferably selected from among fabrics, cloths, foams, meshes, elastomers and combinations thereof. A most preferred material of the sleeve tensioning flap 26, at least in part, is an elastically stretchable synthetic cloth such as nylon or the like. In any case, the material or materials of the sleeve tensioning flap 26 may be the same or different from the material of the main body 24.

The sleeve tensioning flap 26 has a second side 72 opposite the pivot side 68 which is free and unattached when the sleeve tensioning flap 26 is in an inoperative position. The second side 72 of the sleeve tensioning flap 26 is alternately termed a medial side or tab side because the upper and lower sleeve flap tabs 36, 38 on the second side 72 of the sleeve tensioning flap 26 extend to the medial portion of the main body 24 in a manner described below when the knee brace 10 is operatively mounted on a user's leg. The sleeve tensioning flap 26 also has upper and lower edges which are likewise free, i.e., unattached, when the knee sleeve 12 is spread out flat. The upper and lower sleeve flap tabs 36, 38 are integral with or attached to the tab side 72 of the sleeve tensioning flap 26 and extend in a direction opposite the pivot side 68. The upper and lower sleeve flap tabs 36, 38 are vertically spaced apart from one another along the tab side 72 and the intervening segment of the tab side 72 extending between the upper and lower sleeve flap tabs 36, 38 has a concave arcuate shape. An indentation results from the concave arcuate shape of the intervening segment which enables the user to operatively position the sleeve tensioning flap 26 on the knee of the user in a manner described below without the sleeve tensioning flap 26 substantially overlapping engaging the underlying patella.

Each upper and lower sleeve flap tab 36, 38 has an approximately hemispherical configuration. The upper sleeve flap tab 36 is preferably sized to approximate at least the majority, if not substantially the entirety, of the height of the upper half of the main body 24. The lower sleeve flap tab 38 is similarly preferably sized to approximate at least the majority, if not substantially the entirety, of the height of the lower half of the main body 24. The upper sleeve flap tab 36 has an end which is termed an upper tab attachment tip 74 and the lower sleeve flap tab 38 likewise has an end termed a lower tab attachment tip 76. Each upper and lower tab attachment tip 74, 76 is preferably provided with a releasable fastener. A preferred releasable fastener is the hook or loop material of a hook-and-loop fastener. In the present embodiment, the entire inside face of each upper and lower tab attachment tip 74, 76 is covered with the hook material of a hook-and-loop fastener.

Releasable fasteners which are cooperative with the releasable fasteners of the upper and lower tab attachment tips 74, 76 are preferably provided on the outside face of the medial portion of the main body 24. As shown in the embodiment of FIG. 3, the upper half of the outside face of the medial portion of the main body 24 has an upper attachment site 78 affixed thereto by conventional attachment means such as sewing. The upper attachment site 78 is a patch of the loop material cooperative with the hook material of the upper tab attachment tip 74. The lower half of the outside face of the medial portion of the main body 24 similarly has a lower attachment site 80 affixed thereto which is likewise a patch of the loop material cooperative with the hook material of the lower tab attachment tip 76. It is also within the scope of the present invention to omit the patches and integrate the loop material directly into the material of the outside face of the medial portion of the main body 24 so that the outside face itself is an integral upper and lower attachment site. It is likewise within the scope of the present invention to reverse the positions of the hook material and the loop material on the upper and lower sleeve flap tabs 36, 38 and on the outside face of the medial portion of the main body 24 respectively. In any case, the releasable fasteners on the upper and lower tab attachment tips 74, 76 and on the upper and lower attachment sites 78, 80 enable the user to releasably attach the sleeve tensioning flap 26 to the outside face of the medial portion of the main body 24.

The buttress retention flap 20, which includes the upper and lower buttress straps 52, 54, is preferably a shaped sheet of pliant material attached to and extending from the lateral portion of the main body 24 of the knee sleeve 12. In particular, the buttress retention flap 20 has a first side 82 which is attached to the outside face of the lateral portion of the main body 24 along the same lateral joint 70 that attaches the sleeve tensioning flap 26 to the lateral portion of the main body 24. The first side 82 of the buttress retention flap 20 is alternately termed a lateral side or a pivot side because the buttress retention flap 20 is freely rotatable about the pivot side 82 and lateral joint 70 when the buttress retention flap 20 is in the inoperative position. It is alternatively within the scope of the present invention to attach the buttress retention flap 20 to the main body 24 along an alternate longitudinal joint at a lateral position proximal to the lateral position of the lateral joint 70 shown herein.

FIGS. 1 and 3 show the buttress retention flap 20 in its operative position extending from the lateral joint 70 on the lateral portion of the main body 24 and wrapping counterclockwise around the anterior portion of the main body 24 to the medial portion of the main body 24. It is noted that the sleeve tensioning flap 26 overlies the majority, and preferably substantially the entirety, of the buttress retention flap 20 when both are in their operative positions with the knee brace 10 operatively mounted on a user's leg. Attaching the pivot side 82 of the buttress retention flap 20 to the main body 24 is effected in either a substantially permanent manner, e.g., by sewing, or in a selectively releasable manner, e.g., by hook-and-loop fasteners. Attachment is preferably effected by sewing the edge of the pivot 82 to the main body 24 along the lateral joint 70 to form a seam as shown in FIG. 2 or along an alternate joint as described above.

The pliant material for constructing the buttress retention flap 20 is preferably selected from among fabrics, cloths, foams, meshes, elastomers and combinations thereof. A most preferred material of the buttress retention flap 20 is pliant and substantially non-stretchable and, more particularly, is in part or in whole a substantially non-stretchable synthetic fiber mesh and/or is in part or in whole a substantially non-stretchable synthetic cloth such as a substantially non-stretchable nylon or the like. The term substantially non-stretchable is defined herein as encompassing materials which are substantially less stretchable than stretchable materials, i.e., exhibit at most only an insignificant degree of elastic deformation when subjected to usual stretching forces.

An upper slit 84 and a lower slit 86 are provided in the pivot side 68 of the buttress retention flap 20 adjacent to the lateral joint 70. The upper and lower slits 84, 86 enable the intersecting ends 56, 58 of the lateral upper and lower longitudinal members 40, 42 to freely pass through the buttress retention flap 20 and enable the lateral hinge 44 to reside on the outside of the buttress retention flap 20 so that the buttress retention flap 20 does not impede operation of the lateral hinge 44.

The buttress retention flap 20 has a second side 88 opposite the pivot side 82 which is free and unattached when the buttress retention flap 20 is in an inoperative position. The second side 88 of the buttress retention flap 20 is alternately termed a medial side or strap side because the upper and lower buttress straps 52, 54 on the second side 88 of the buttress retention flap 20 extend to the medial portion of the main body 24 in a manner described below when the knee brace 10 is operatively mounted on a user's leg. The buttress retention flap 20 also has upper and lower edges which are likewise free, i.e., unattached, when the knee sleeve 12 is spread out flat. The upper and lower buttress straps 52, 54 are integral with or attached to the strap side 88 of the buttress retention flap 20 and extend in a direction opposite the pivot side 82. In particular, the upper buttress strap 52 extends at an upward angle away from the strap side 88 to an attachment end 90 of the upper buttress strap 52, while the lower buttress strap 54 extends away at a downward angle to an attachment end 92 of the lower buttress strap 54, such that the buttress retention flap 20, having the upper and lower buttress straps 52, 54 extending therefrom, resembles a V-shape. The upper and lower buttress straps 52, 54 are vertically spaced apart from one another along the strap side 88 and the intervening segment of the strap side 88 extending between the upper and lower buttress straps 52, 54 has a concave arcuate shape similar to the tab side of the sleeve tensioning flap 26. The resulting indentation enables the user to operatively position the buttress retention flap 20 on the knee of the user in a manner described below without the buttress retention flap 20 substantially overlapping the underlying patella.

Each upper and lower buttress strap 52, 54 is preferably provided with a releasable fastener. A preferred releasable fastener is the hook or loop material of a hook-and-loop fastener. In the present embodiment, the attachment ends 90, 92 of the upper and lower buttress straps 52, 54 are alternatively termed upper and lower strap attachment tips respectively. The upper and lower strap attachment tips 90, 92 have inside faces which are covered with the hook material of a hook-and-loop fastener which is preferably integral with the material of the upper and lower strap attachment tips 90, 92. The outside faces of the upper and lower buttress straps 52, 54 are covered or integral with the loop material of a hook-and-loop fastener which is cooperative with the hook material of the upper and lower strap attachment tips 90, 92.

Figure 5:
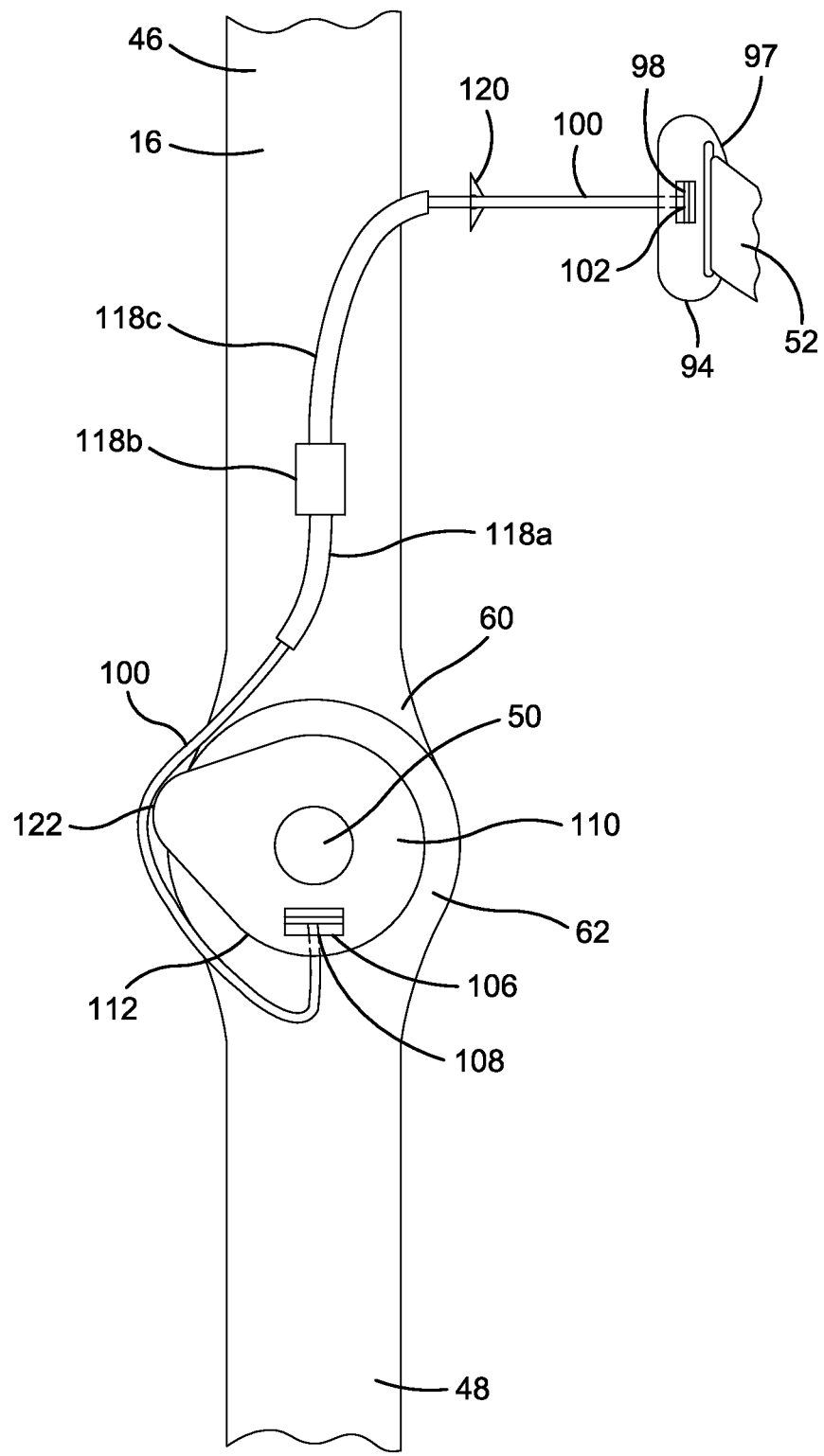
FIG. 5 is a conceptualized view from the rear of a tensioning line path for the knee brace of FIG. 1 when the knee is in a position of full extension.

The knee brace 10 further includes an upper connective member 94 and a lower buttress strap retainer 96 shown in FIG. 3 which cooperate with the upper and lower buttress straps 52, 54 to enable the user to releasably connect the buttress retention flap 20 to the medial side of the knee brace 10. Referring additionally to FIG. 5, the upper connective member 94 is a single unitary body which comprises an upper buttress strap retainer 97 and an upper tensioning line anchor 98 integrally formed and integrally attached to one another. A preferred material of the upper connective member 94 is a rigid or semi-rigid plastic.

In accordance with the present embodiment, the upper buttress strap retainer 97 is a strap retention loop formed in the body of the upper connective member 94 which is sized and configured to receive the upper buttress strap 52 and to enable unimpeded slidable passage of the upper buttress strap 52 therethrough. The upper tensioning line anchor 98 includes a horizontal bore and an interior locking chamber likewise formed in the body of the upper connective member 94. The horizontal bore extends from the posterior face of the body into the interior locking chamber. As such, the horizontal bore provides an unobstructed channel from the exterior to the locking chamber. The horizontal bore is configured and sized to slidably receive a tensioning line 100 and, more particularly, an upper anchored end 102 of the tensioning line 100. The locking chamber is configured and sized to lock the upper anchored end 102 therein, thereby fixably securing the upper anchored end 102 of the tensioning line 100 to the upper tensioning line anchor 98 and correspondingly to the upper connective member 94, in which the upper tensioning line anchor 98 is integrally formed.

Although not shown, it is alternatively within the scope of the present invention to construct the upper buttress strap retainer and the upper tensioning line anchor as separate distinct structural bodies. In accordance with this embodiment, it is nevertheless preferable to position the upper buttress strap retainer and upper tensioning line anchor side by side at substantially the same location as the upper connective member 94 and likewise preferable to permanently or releasably rigidly attach or otherwise rigidly connect the upper buttress strap retainer and upper tensioning line anchor to one another so that the structurally distinct, but interconnected, upper buttress strap retainer and upper tensioning line anchor function as a single integrated unitary structure in substantially the same manner as the upper connective member 94 described herein which integrally includes the upper buttress strap retainer 97 and upper tensioning line anchor 98.

The tensioning line 100 is a strong lightweight thin flexible material in the form of a string, cord, wire, cable, or the like. A preferred tensioning line 100 of the present embodiment is a non-stretchable, small diameter, high-strength fiber-filament cord having a low friction surface that offers little frictional resistance when sliding the tensioning line 100 through the horizontal bore. In accordance with one embodiment, the tensioning line 100 is highly pliant or pliable. In accordance with another embodiment, the tensioning line 100 is less pliant and is somewhat inelastic and stiff, yet is still flexible, which enables the tensioning line 100 to be inelastically deformed, e.g., manually bent, into different shapes if desired, but also enables it to be manually straightened thereafter if desired. This characteristic can advantageously facilitate fixable locking of the upper anchored end 102 into the upper tensioning line anchor 98.

Locking the upper anchored end 102 of the tensioning line 100 in substantially permanent fixed attachment to the upper tensioning line anchor 98 can be effected by any number of means. In accordance with the present embodiment, the upper anchored end 102 of the tensioning line 100 is threaded through the horizontal bore of the upper tensioning line anchor 98 in the anterior direction until the upper anchored end 102 and a segment of the tensioning line 100 extend into the locking chamber. The upper anchored end 102 can then be substantially permanently fixably secured in the locking chamber by means such as knotting the upper anchored end 102 onto itself so that the resulting knot on the upper anchored end 102 is much larger than the cross-section of the horizontal bore, thereby preventing the upper anchored end 102 from passing out of the locking chamber and back through the horizontal bore. Alternatively, a post or some other anchoring structure can be provided in the locking chamber, to which the upper anchored end 102 can be knotted, tied to, wrapped around or otherwise substantially permanently fixably attached to, thereby preventing the upper anchored end 102 from passing back out of the locking chamber.

The above-described upper tensioning line anchor 98 is but one embodiment of a structure for substantially fixably permanently anchoring the upper anchored end 102 of the tensioning line 100. Other conventional structures for performing this function of fixably locking or securing the upper anchored end 102 of the tensioning line 100 to an anchor are readily within the purview of the ordinary artisan and are within the scope of the present invention. In any case, the upper connective member 94 (including the upper buttress strap retainer 97 and upper tensioning line anchor 98), the upper buttress strap 52 and the buttress retention flap 20 in series provide a connective linkage between the upper anchored end 102 of the tensioning line 100 and the buttress 18.

The lower buttress strap retainer 96 has a construction similar to the upper buttress strap retainer 97, but lacks an integral tensioning line anchor. As such, the lower buttress strap retainer 96 is a strap retention loop which is sized and configured to receive the lower buttress strap 54 and to enable unimpeded slidable passage of the upper buttress strap 54 therethrough. The lower buttress strap retainer 96 is substantially fixably permanently attached to the outside face of the medial portion of the main body 24 by conventional attachment means, thereby fixing the position of the lower buttress strap retainer 96 relative to the main body 24. This is in contrast to the upper connection member 94 (and correspondingly the upper buttress strap retainer 97 and upper tensioning line anchor 98), which is variably positionable relative to the main body 24 because the upper connection member 94 is connected to the main body 24 via the tensioning line 100, which is likewise variably positionable relative to the main body 24 as described below. In the present embodiment, permanent fixed attachment of the lower buttress strap retainer 96 to the main body 24 is effected by sewing it along a common seam with the lower attachment patch 80. Alternatively, the lower buttress strap retainer 96 can be sewn to the main body 24 independent of the lower attachment patch 80.

Releasable connection of the buttress retention flap 20 to the tensioning line 100 and outside face of the medial portion of the main body 24 is effected by threading the upper and lower strap attachment tips 90, 92 through the strap retention loops of the upper and lower buttress strap retainers, 97, 96 respectively. The upper and lower buttress straps 52, 54 are then doubled back over themselves to a selected point on the outside face of the mid-section of the upper and lower buttress straps 52, 54, which is termed the releasable strap attachment point. The upper and lower strap attachment tips 90, 92 are releasably fastened to the respective releasable strap attachment point by means of the hook-and-loop fasteners. The length of the doubled back segment of the upper and lower buttress straps 52, 54 is termed the overlap length and determines the overall length of the upper and lower buttress straps 52, 54 and correspondingly their tightness.

In particular, decreasing the overlap length of the upper and lower buttress straps 52, 54 by releasably fastening the upper and lower strap attachment tips 90, 92 to a releasable strap attachment point on the outside face of the upper and lower buttress straps 52, 54 closer to the upper and lower buttress strap retainers 97, 96 respectively increases the overall length of the upper and lower buttress straps 52, 54, thereby loosening the upper and lower buttress straps 52, 54. Increasing the overlap length of the upper and lower buttress straps 52, 54 by releasably fastening the upper and lower strap attachment tips 90, 92 to a releasable strap attachment point on the outside face of the upper and lower buttress straps 52, 54 farther from the upper and lower buttress strap retainers 97, 96 respectively decreases the overall length of the upper and lower buttress straps 52, 54, thereby tightening the upper and lower buttress straps 52, 54.

In view of the above description, a preferred method for operatively mounting the knee brace 10 on a user's leg can be summarized by the following sequential steps:
(1) mounting the main body 24 of the knee sleeve 12 on the leg;
(2) medially connecting the buttress retention flap 20 to the tensioning line 100 and main body 24;
(3) adjusting the tightness of the buttress retention flap 20;
(4) medially attaching the sleeve tensioning flap 26 to the main body 24; and
(5) adjusting the tension of the sleeve tensioning flap 26.

Describing these steps with greater particularity, step 1 is performed by placing the user's foot through the top opening of the knee sleeve 12 and sliding the knee sleeve 12 up over the knee causing the user's foot to extend out the bottom opening of the knee sleeve 12 and the lateral and medial hinges 44, 50 of the knee brace 10 to align with the knee.

Step 2 is performed by manually grasping the upper and lower strap attachment tips 90, 92 of the upper and lower buttress straps 52, 54 and manually pulling the buttress retention flap 26 anteriorly (see directional arrows in FIG. 2), which is the same anterior direction the buttress retention flap 26 extends in FIG. 2, until the upper and lower strap attachment tips 90, 92 align with the upper and lower buttress strap retainers 97, 96 respectively threading the upper and lower strap attachment tips 90, 92 through the strap retention loops of the upper and lower buttress strap retainers 97, 96 respectively pulling the upper and lower buttress straps 52, 54 through the strap retention loops to double the upper and lower buttress straps 52, 54 back over themselves a given overlap length and attaching doubled over upper and lower strap attachment tips 90, 92 to the underlying releasable strap attachment point on the upper and lower buttress straps 52, 54 respectively.

Step 3 is performed by adjusting the overlap length of the upper and lower buttress straps 52, 54. Increasing the overlap length, increases the tightness of the buttress retention flap 20, while decreasing the overlap length, decreases the tightness of the buttress retention flap 20. By increasing or decreasing the tightness of the buttress retention flap 20, the user correspondingly adjusts the position of the buttress 18 on the leg. It is apparent that the tightness of the buttress retention flap 20 and correspondingly the position of the buttress 18 can be readjusted any number of times simply by repeating step 3.

It is noted that when the upper and lower strap attachment tips 90, 92 are releasably attached to the underlying releasable strap attachment point on the upper and lower buttress straps 52, 54 and the tension of the buttress retention flap 20 is desirably adjusted, the arcuate edge on the strap side 88 of the buttress retention flap 20 preferably anteriorly aligns adjacent to, but not in contact with, the patella of the knee, which lies under and is completely covered over by the anterior portion of the main body 24.

Step 4 is performed by manually grasping the upper and lower tab attachment tips 74, 76 and manually pulling the sleeve tensioning flap 26 anteriorly (see directional arrows in FIGS. 2 and 3) to pass over the lateral portion and wrap around to the medial portion of the main body 24. The user pulls on the sleeve tensioning flap 26 until the upper and lower tab attachment tips 74, 76 align with the upper and lower attachment sites 78, 80 and releasably fastens the upper and lower tab attachment tips 74, 76 thereto.

Step 5 is performed by manually releasing attachment of the upper and lower tab attachment tips 74, 76 to the upper and lower attachment sites 78, 80 and reattaching the upper and lower tab attachment tips 74, 76 to the upper and lower attachment sites 78, 80 at different points thereon. In particular, reattaching the upper and lower tab attachment tips 74, 76 to the upper and lower attachment sites 78, 80 at a more posterior point thereon increases the tension of the sleeve tensioning flap 26 and correspondingly tightens the knee sleeve 12 on the user's leg. Reattaching the upper and lower tab attachment tips 74, 76 to the upper and lower attachment sites 78, 80 at a more anterior point thereon decreases the tension of the sleeve tensioning flap 26 and correspondingly loosens the knee sleeve 12 on the user's leg. It is apparent that the tension of the sleeve tensioning flap 26 and correspondingly the tightness of the knee sleeve 12 on the user's leg can be readjusted any number of times simply by repeating step 5.

It is noted that when the upper and lower sleeve flap tabs 74, 76 are releasably attached to the upper and lower attachment sites 78, 80 and the tension of the sleeve tensioning flap 26 is desirably adjusted, the sleeve tensioning flap 26 preferably covers the underlying buttress retention flap 20. The arcuate edge on the tab side 72 of the sleeve tensioning flap 26 also preferably anteriorly aligns with the arcuate edge on the strap side 88 of the underlying buttress retention flap 20 as well as adjacent to, but not in contact with, the patella of the knee, which lies under and is completely covered over by the anterior portion of the main body 24.

Referring additionally to FIGS. 4-7, the buttress 18 and tensioning line 100 cooperatively provide the knee brace 10 with specific desirable performance characteristics for the treatment of patellar tracking disorders. The buttress 18 is a narrow elongate member which has a substantially straight anterior longitudinal edge 104. The anterior longitudinal edge 104, which is the edge closest to the knee when the knee brace 10 is in the operative position, although substantially straight, is preferably provided with a slight arc. The arc of the anterior longitudinal edge 104, if any, typically has even less curvature than the limited curvature of the strap side 88 and tab side 72 of the buttress retention flap 20 and sleeve tensioning flap 26 respectively. Representative dimensions of a buttress having utility in the knee brace 10, which are recited herein by way of example rather than by way of limitation, are: about 4 inches in length, about 1 inch in width, and about 0.5 inches in thickness.

The buttress 18 is formed from a material, such as a foam, which has flexion and compression resistant properties, yet is preferably capable of some degree of flexion and compression. A preferred material of the buttress 18 preferably compresses at least 25% to provide desirable proprioception for joint awareness when the buttress 18 is operatively positioned in abutment with the leg of a user and is subjected to the operating forces of the knee brace 10 during normal daily user activity. As such, the buttress 18 provides a degree of proprioception, cushioning and comfort to a user of the knee brace 10 while the buttress performs its intended knee treatment function. A thin plate of stiffer, less flexible material, such as a semi-rigid, relatively incompressible plastic, which is cut to substantially the same footprint as the cushioning material, may be removably or permanently joined to the anterior face of the cushioning material to add greater stiffness to the buttress 18 without diminishing the cushioning effect of the buttress 18 to the user.

The buttress 18 is fixably positioned on the inside face of the buttress retention flap 20. In a preferred position, the anterior longitudinal edge 104 of the buttress 18 is slightly offset posteriorly from the edge of the strap side 88 of the buttress retention flap 20, but the anterior longitudinal edge 104 of the buttress 18, nevertheless, substantially parallelly tracks the edge of the strap side 88 of the buttress retention flap 20. In accordance with the present embodiment, the buttress 18 is retained against the inside face of the buttress retention flap 20 by overlaying a similarly shaped and slightly oversized piece of cloth (not shown) atop the buttress 18 as the buttress 18 sits in a desired position atop the inside face of the buttress retention flap 20. The perimeter of the cloth is sewn to the material of the buttress retention flap 20, thereby creating a pouch or pocket against the buttress retention flap 20 which retains the buttress 18 therein.

The upper tensioning line anchor 98, which is integrally formed with the upper buttress strap retainer 97 in the unitary upper connection member 94, is described above as anchoring the upper anchored end 102 of the tensioning line 100 by fixably attaching the upper anchored end 102 in the upper tensioning line anchor 98. Referring specifically to FIGS. 4 and 5, a lower tensioning line anchor 106 similarly anchors an opposite lower anchored end 108 of the tensioning line 100.

The lower tensioning line anchor 106 is integrally formed with a tensioning line cam 110 in a combined single unitary structure which is positioned proximal to the medial longitudinal support assembly 16. The tensioning line cam 110 is a rotational body having a plate-like structure. The peripheral shape of the tensioning line cam 110 approximates a circle, but is eccentric or irregular in its roundness, i.e., is somewhat out-of-round which defines it as a cam. The circumference of the tensioning line cam 110 defines an arcuate operating surface 112 having a width which approximately corresponds to the thickness of the tensioning line cam 110. The tensioning line cam 110 is preferably constructed from a rigid or semi-rigid plastic such as the same material from which the lateral and medial longitudinal support assemblies 14, 16 is formed.

In accordance with the present embodiment, the tensioning line cam 110 has thin disc-like inside and outside faces 114, 116 positioned on opposing sides of the operating surface 112 of the tensioning line cam 110. The operating surface 112 is oriented substantially orthogonal to the inside and outside faces 114, 116 which have circumferences slightly oversized relative to the circumference of the operating surface 112 so that the faces 114, 116 form sidewalls to the operating surface 112. The distance between the sidewalls defines the precise width of the operating surface 112 and is sufficient to enable the sidewalls to receive the tensioning line 100 between them. As such, the sidewalls of the inside and outside faces 114, 116 advantageously assist in retaining the tensioning line 100 in engagement with the operating surface 112. In particular, the sidewalls of the inside and outside faces 114, 116 prevent the tensioning line 100 from coming out of its designated tensioning line path along the operating surface 112. In the interest of clarity, the inside and outside faces 114, 116 have been omitted from FIGS. 3 and 5-7 and are only shown in FIG. 4. Although also not shown, it is alternatively within the scope of the present invention to integrally construct the tensioning line cam 110 and the intersecting end 62 of the medial lower longitudinal member 48 as a single unitary structure such that the tensioning line cam is simply a continuous inward extension of the intersecting end 62.

In any case, the lower tensioning line anchor 106, which is integral with the tensioning line cam 110, has a radial bore extending from the operating surface 112 of the tensioning line cam 110 into a locking chamber in the interior of the tensioning line cam 110 proximal to the operating surface 112. The radial bore provides an unobstructed channel from the exterior to the locking chamber. The radial bore is configured and sized to slidably receive the lower anchored end 108 of the tensioning line 100 and the locking chamber is configured and sized to fixably lock the lower anchored end 108 therein, thereby fixably securing the lower anchored end 108 of the tensioning line 100 to the integral lower tensioning line anchor 106 and tensioning line cam 110. Fixably locking the lower anchored end 108 of the tensioning line 100 in substantially permanent attachment to the lower tensioning line anchor 106 may be effected in substantially the same manner as described above with respect to the upper anchored end 102 of the tensioning line 100 and the upper tensioning line anchor 98.

The tensioning line cam 110 is coupled with the medial lower longitudinal member 48 by engaging the outside face of the tensioning line cam 110 with the inside face of the intersecting end 62 of the medial lower longitudinal member 48 and fixably attaching them to one another. Fixable attachment of the tensioning line cam 110 to the intersecting end 62 is effected at least in part by extending the medial hinge 50 through the center of the tensioning line cam 110 and substantially permanently attaching the medial hinge 50 to the inside face of the tensioning line cam 110, thereby forming a stacked structure 46, 48, 110 shown in FIG. 4. As a result, the integral lower tensioning line anchor 106 and tensioning line cam 110 provide a connective linkage between the lower anchored end 108 of the tensioning line 100 and the medial longitudinal support assembly 16.

In accordance with the present embodiment, the medial upper and lower longitudinal members 46, 48 remain freely rotatable relative to one another in the stacked structure 46, 48, 110. The tensioning line cam 110 is likewise freely rotatable relative to the medial upper longitudinal member 46, but the tensioning line cam 110 is fixed relative to the medial lower longitudinal member 48. Accordingly, the tensioning line cam 110 rotates in identical correspondence with rotation of the medial lower longitudinal member 48.

It is apparent that the tensioning line cam 110 defines, in part, the tensioning line path that the tensioning line 100 travels between upper and lower tensioning line anchors 98, 106 to which the upper and lower ends 102, 108 of the tensioning line 100 are fixably secured or locked. In addition to the tensioning line cam 110, the tensioning line path further includes a multi-segmented tensioning line guide 118a, 118b, 118c. The segments of the tensioning line guide, i.e., lower segment 118a, middle segment 118b, and upper segment 118c, are serially aligned along the inside face of the medial upper longitudinal member 46. The middle segment 118*b* of the tensioning line guide is a substantially rigid, semi-rigid or semi-flexible structure having a relatively straight configuration with a central longitudinal bore extending therethrough which is configured and sized to receive the tensioning line 100 and to permit unimpeded slidable passage of the tensioning line 100 therethrough. The middle segment 118*b* is fixably attached to the inside face of the medial upper longitudinal member 46 at an intermediate point about midway along the length of the medial longitudinal axis of the medial upper longitudinal member 46 with the central longitudinal bore of the middle segment 118*b* aligned with the medial longitudinal axis.

Each of the lower and upper segments 118*a*, 118*c* is preferably a length of stiffened semi-flexible tubing. Although preferably less flexible than the tensioning line 100, the lower and upper segments 118*a*, 118*c* of the tensioning line guide are, nevertheless, preferably flexed into an arcuate configuration. Each lower and upper segment 118*a*, 118*c* likewise has a central bore extending therethrough which is configured and sized to receive the tensioning line 100 and to permit unimpeded slidable passage of the tensioning line 100 therethrough. The top of the lower segment 118*a* of the tensioning line guide is positioned at the medial longitudinal axis on the inside face of the medial upper longitudinal member 46 immediately below the bottom of the middle segment 118*b* of the tensioning line guide. The lower and middle segments 118*a*, 118*b* are preferably attached to one another, with the central bores of the lower and middle segments 118*a*, 118*b* aligned. The bottom of the lower segment 118*a* of the tensioning line guide is positioned in proximal correspondence with the operating surface 112 of the tensioning line cam 110 so that the tensioning line 100 essentially passes directly from the operating surface 112 to the central bore of the lower segment 118*a* with, at most, only a short segment of the tensioning line 100 being exposed between the operating surface 112 and lower segment 118*a*. It is also noted that the bottom of the lower segment 118*a* of the tensioning line guide is positioned in close proximity to the intersecting ends 60, 62 of the medial upper and lower longitudinal members 46, 48 and the medial hinge 50.

The bottom of the upper segment 118*c* of the tensioning line guide is positioned at the medial longitudinal axis on the inside face of the medial upper longitudinal member 46 immediately above the top of the middle segment 118*b* of the tensioning line guide. The middle and upper segments 118*b*, 118*c* are preferably attached to one another, with the central bores of the middle and upper segments 118*b*, 118*c* aligned. The top bore of the upper segment 118*c* of the tensioning line guide is positioned in proximal correspondence with a tensioning line port 120 extending through the main body 24 so that the tensioning line 100 essentially passes directly from the upper segment 118*c* to the tensioning line port 120 with, at most, only a short segment of the tensioning line 100 being exposed between the upper segment 118*c* and tensioning line port 120. It is further within the scope of the present invention to extend the top of the upper segment 118*c* all the way into the port 120 or even somewhat therethrough, in which case none of the tensioning line 100 is exposed as it passes into and through the tensioning line port 120. It is also noted that the top of the upper segment 118*c* of the tensioning line guide is positioned proximal to the upper end of the medial upper longitudinal member 46.

In summary, the tensioning line path has two terminuses with one terminus being the lower tensioning line anchor 106. The tensioning line path extends radially outward from the interior locking chamber of the lower tensioning line anchor 106 via the radial bore onto the operating surface 112 of the tensioning line cam 110. The tensioning line path follows the operating surface 112 on the posterior peripheral circumference of the tensioning line cam 110 in an upward rotational direction until the tensioning line path reaches the bottom of the lower segment 118*a* of the tensioning line guide which corresponds to a lower posterior position on the inside face of the medial upper longitudinal member 46. The lower, middle and upper segments 118*a*, 118*b*, 118*c* of the tensioning line guide in combination define an "S"-shaped segment of the tensioning line path.

The lower segment 118*a* is anteriorly curved as it extends from its bottom to its top, thereby directing the tensioning line path from the posterior edge on the lower inside face of the medial upper longitudinal member 46 anteriorly and upwardly along a lower length of the inside face of the medial upper longitudinal member 46. The tensioning line path continues in correspondence with the central bore of the lower segment 118*a* until the tensioning line path reaches the intermediate point along the medial longitudinal axis on the inside face of the medial upper longitudinal member 46 which corresponds to the position of the bottom of the middle segment 118*b* of the tensioning line guide as well as the top of the lower segment 118*a*.

The tensioning line path continues in succession through the central bores of the middle and upper segments 118*b*, 118*c* of the tensioning line guide which are likewise positioned along the inside face of the medial upper longitudinal member 46. The central bore of the middle segment 118*b* is relatively straight and corresponds to the medial longitudinal axis of the medial upper longitudinal support 46. The central bore of the upper segment 118*c* is likewise anteriorly curved as it extends from its bottom to its top, thereby directing the tensioning line path from the medial longitudinal axis on the intermediate inside face of the medial upper longitudinal member 46 anteriorly and upwardly along an upper length of the inside face of the medial upper longitudinal member 46. The tensioning line path continues in correspondence with the central bore of the upper segment 118*c* until the tensioning line path reaches the anterior edge on the upper inside face of the medial upper longitudinal member 46 which corresponds to a position proximal to the tensioning line port 120 as well as the top of the upper segment 118*c*.

The tensioning line port 120 is a pair of serially aligned openings in the medial upper pocket 32 and the outside face of the upper medial portion of the main body 24 of the knee sleeve 12 immediately anterior of the medial upper longitudinal member 46. The tensioning line path extends anteriorly through the tensioning line port 120 into the medial upper pocket 32 after exiting the top of the upper segment 118*c* in the case where the upper segment 118*c* does not extend into or through the tensioning line port 120 or while still within the central bore of the upper segment 118*c* in the case where the upper segment 118*c* extends into or through the tensioning line port 120. In any case, the tensioning line path extends anteriorly from the tensioning line port 120 to the upper connective member 94 including the upper tensioning line anchor 98 which is anteriorly positioned adjacent to the tensioning line port 120. The upper tensioning line anchor 98 is the other terminus of the tensioning line path. As such, the tensioning line path extends into the interior of the upper tensioning line anchor 98 and, more particularly, into the locking chamber of the upper tensioning line anchor 98 via the horizontal bore where the upper anchored end 102 of the tensioning line 100 is received and fixably locked therein.

It is noted that when the knee brace 10 is operatively mounted on the leg of a user, the knee brace 10 preferably maintains the tensioning line 100 taut and substantially free of slack within the above-described tensioning line path at all times of knee brace operation while the user performs full range of motion activity with the knee. At the same time, the knee brace 10 desirably functions to automatically variably self-adjust the tension of the tensioning line 100 and interconnected components of the knee brace 10 in response to changes in the orientation angle of the knee due to flexion or extension of the knee in accordance with the following method of operation.

Referring to the FIGS. 1-5, the knee brace 10 is mounted in the manner described above on a leg of a user for which patellar stabilization and patellofemoral joint tracking is desired. In particular, the knee sleeve 12 is pulled over the leg until the lateral and medial hinges 44, 50 are appropriately positioned in alignment with the respective lateral and medial condyles of the knee, the upper part of the knee sleeve 12 encloses the upper leg immediately above the knee and the lower part of the knee sleeve encloses the lower leg immediately below the knee. With the knee sleeve 12 in place and the upper and lower buttress straps 52, 54 loosely threaded through the strap retention loops of the upper and lower buttress strap retainers 97, 96, the user positions the buttress 18 to the lateral side of the knee with the buttress 18 resting on the lateral side of the head of the femur and/or the surrounding soft tissue. While positioning the buttress 18, the user takes care to ensure that the anterior longitudinal edge 104 of the buttress 18 maintains a physical separation from the patella such that a space exists between them. In sum, the buttress 18 is positioned so that it does not overlap or otherwise laterally engage the patella.

While manually holding the buttress 18 in its desired position, the user adjusts the length of the upper and lower buttress straps 52, 54. In particular, the user releasably fastens the upper and lower strap attachment tips 90, 92 in the manner described above to set the lengths and correspondingly the tension of the upper and lower buttress straps 52, 54 at a level which is sufficient to cause the buttress retention flap 20 to anteriorly extend from the lateral side of the leg and apply a sufficient degree of radial compression force against the buttress 18 to retain the buttress 18 in its desired position against the lateral side of the knee, but off of the patella, when the user manually releases the buttress 18.

The user desirably takes care not to set the tension of the upper and lower buttress straps 52, 54 at an excessive level which would correspondingly cause the buttress retention flap 20 to apply an excessive degree of compression force against the buttress 18, thereby negatively impacting normal movement of the knee or operation of the knee brace 10 or causing the buttress 18 to directly engage the patella. The user also desirably takes care in setting the lengths of the upper and lower buttress straps 52, 54 to ensure that the upper buttress strap 52 passes over the knee along a linear upper strap path above the patella and the lower buttress strap 54 passes over the knee along a linear strap path below the patella so that neither buttress strap 52, 54 contacts or otherwise adversely engages the anterior face of the patella during operation of the knee brace 10. In particular, the user takes care in setting the lengths of the upper and lower buttress straps 52, 54 to ensure that the buttress retention flap 20 and included upper and lower buttress straps 52, 54 do not contact or otherwise adversely engage the anterior face of the patella when the upper and lower buttress straps 52, 54 are drawn across the anterior side of the leg to the medial side during mounting and operation of the knee brace 10.

Upon securing the upper and lower strap attachment tips 90, 92, the knee brace 10 maintains the set lengths of the upper and lower buttress straps 52, 54 fixed during knee brace operation while the knee undergoes range of motion activity. However, the user can pause knee brace operation and knee range of motion activity at any time to readjust the lengths of the upper and lower buttress straps 52, 54 from their set length if needed or desired while the knee brace 10 remains in place on the knee in a manner described above to tighten or loosen the upper and lower buttress straps 52, 54 and correspondingly to increase or decrease the compression force of the buttress retention flap 20 on the buttress 18.

Having set the lengths of the upper and lower buttress straps 52, 54, the user anteriorly wraps the sleeve tensioning flap 26 across the lateral side of the leg and releasably fastens the upper and lower tab attachment tips 74, 76 of the upper and lower sleeve flap tabs 36, 38 to the upper and lower attachment sites 78, 80 in the manner described above. In particular, the user selects points on the upper and lower attachment sites 78, 80 at which to releasably fasten the upper and lower tab attachment tips 74, 76, thereby setting the tension of the sleeve tensioning flap 26 at a desired level causing the sleeve tensioning flap 26 to apply a desired degree of radial compression force to the leg. The user also takes care in selecting the points on the upper and lower attachment sites 78, 80 at which to releasably fasten the upper and lower tab attachment tips 74, 76 to ensure that the sleeve tensioning flap 26 and included upper and lower sleeve flap tabs 36, 38 do not contact or otherwise adversely engage the anterior face of the patella when the upper and lower sleeve flap tabs 36, 38 are stretched across the anterior side of the leg to the medial side during mounting and operation of the knee brace 10.

Upon securing the upper and lower tab attachment tips 74, 76, the knee brace 10 maintains the tension of the sleeve tensioning flap 26 fixed during operation. However, the user can pause knee brace operation and knee range of motion activity at any time to readjust the tension of the sleeve tensioning flap 26 from its set tension if needed or desired while the knee brace 10 remains in place on the knee in a manner described above to increase or decrease the compression force of the sleeve tensioning flap 26 on the leg.

When the user performs range of motion activity with the knee, the knee brace 10 remediates existing disorders in the patellofemoral joint or precludes potential disorders to substantially prevent patellar subluxation or dislocation. This beneficial result is achieved by dynamically tracking the patellofemoral joint. Dynamic tracking is specifically enabled by positioning the buttress 18 relative to the knee and applying a radial compression force across the buttress 18 to a compression surface on the knee in a manner described below. The radial compression force the buttress 18 applies to the compression surface on the knee at the specified position imposes a desired patellar track on the knee when the knee flexes or extends through its normal range of motion. In particular, the position of the buttress 18 and radial compression force of the buttress 18 effectively maintain the patella in the underlying trochlear groove and prevent the patella from migrating in a lateral direction out of the trochlear groove during flexion or extension of the knee. By not overlapping the patella or otherwise substantially contacting the patella as specified herein, the buttress 18 also substantially avoids radial compression of the patella which would undesirably tend to inhibit normal range of motion of the knee and cause pain to the user.

The following describes at least some of the forces generated by the knee brace 10 when it is operatively mounted on the leg of a user. The upper buttress strap 52 and the serially connected tensioning line 100 apply a substantially rotationally-directed tension force to the buttress retention flap 20, which translates this rotational tension force to a radial compression force on the buttress 18. The radial compression force enables the buttress 18 to retain its position against the compression surface at the lateral side of the knee where the buttress 18 transfers the applied radial compression force to the compression surface at the lateral side of the knee without engaging or overlapping the patella. It is advantageous that the position of the tensioning line 100 relative to the knee directs the focus of the tension force to the upper buttress strap 52 which correspondingly directs the focus of the resulting radial compression force to the upper segment of the buttress 18. The upper segment of the buttress 18 in turn directs the focus of the radial compression force to the compression surface at the upper lateral quadrant of the knee including the head of the femur and/or surrounding soft tissue. It is believed that a greater treatment benefit of the knee brace 10 occurs when the buttress 18 focuses its radial compression force to a compression surface on the upper lateral quadrant of the knee and off of the patella. It is further believed that a lesser treatment benefit is achieved when the buttress 18 applies its radial compression force to a compression surface on the lower lateral quadrant of the knee.

An advantageous feature of the knee brace 10 is its ability to automatically self-adjust the tension and corresponding compression forces generated by the knee brace 10 in response to changes in the orientation angle of the knee due to flexion and extension thereof. These self-adjustable forces are summarized as: (1) the tension force that the upper buttress strap 52 and the serially connected tensioning line 100 apply to the buttress retention flap 20 in a substantially rotational direction; (2) the compression force that the buttress retention flap 20 translates from the tensioning force recited above and applies to the buttress 18 in a substantially radial direction; and (3) the compression force corresponding to the compression force recited above that the buttress 18 transfers to the knee in this same substantially radial direction.

The knee has a reference angle of 0° at full extension and the orientation angle of the knee increases from 0° toward 90° and beyond as the knee rotates to full flexion. Automatic force adjustment of the knee brace 10 advantageously occurs when the orientation angle of the knee falls below about 30° while the knee is rotating in the extension direction (i.e., toward 0°). In particular, the knee brace 10 automatically adjusts itself from a lower tension state to a higher tension state when orientation angle of the knee falls below about 30°. At an orientation angle below about 30°, the automatic force adjustment function of the knee brace 10 significantly increases the tension force on the buttress retention flap 20 and the resulting radial compression force of the buttress 18 against the compression surface at the lateral side of the knee.

Automatic force adjustment of the knee brace likewise occurs when the orientation angle of the knee exceeds about 35° while the knee is rotating in the flexion direction (i.e., away from 0° toward 90° or greater). In particular, the knee brace 10 automatically adjusts itself from a higher tension tense state to a lower tension state when the orientation angle of the knee exceeds about 35°. At an orientation angle above about 35°, the automatic force adjustment function of the knee brace 10 significantly decreases the tension force on the buttress retention flap 20 and the resulting radial compression force of the buttress 18 against the compression surface at the lateral side of the knee. Thus, the knee brace 10 has an automatic tension transition point which occurs when the knee, and correspondingly the knee brace 10, pass through an orientation angle in a range between about 30° and 35° in either the flexion or extension direction.

As a result, the buttress 18 is desirably more securely retained against the knee with a greater compression force when the risk of patellar subluxation or dislocation is greater, i.e., during substantial knee extension when the orientation angle of the knee falls below a value of about 30° and preferably is within an angular range of about 30° to 15°. The buttress is desirably less securely retained against the knee with a lower compression force when the risk of patellar subluxation or dislocation is reduced, i.e., during substantial knee flexion when the orientation angle of the knee exceeds a value of about 30° and more preferably about 35°.

Figure 6:
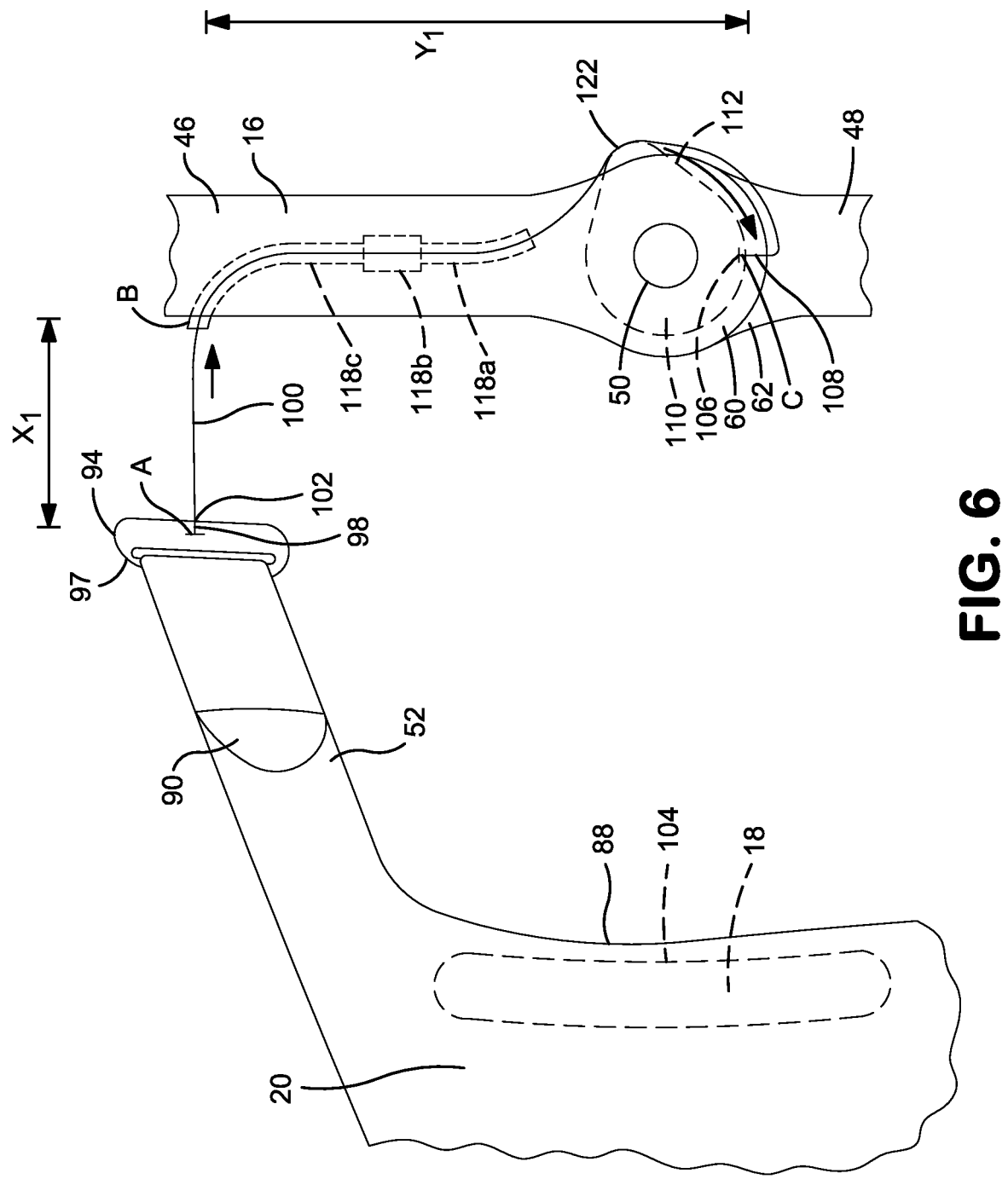
FIG. 6 is a conceptualized view from the front of a tensioning line path for the knee brace of FIG. 1 and its cooperative relation with other elements of the knee brace when the knee is in a position of full extension.

The automatic force adjustment function of the knee brace 10 is further illustrated with reference to FIGS. 6 and 7 which show the outside faces of the brace components therein as distinguished from FIG. 5 which shows the inside faces of the brace components therein. Referring initially to FIG. 6, the knee brace 10 is mounted on the knee with the orientation angle of the knee at 0° in substantially full extension. It is noted that the orientation angle of the knee brace 10 is essentially identical to the orientation angle of the knee throughout full range of motion activity of the knee.

With specific reference to FIG. 6, an upper anchor point for the upper anchored end 102 of the tensioning line 100, which is in the locking chamber of the upper tensioning line anchor 98, is designated A. Point A has a variable position relative to point B which is defined below. The variable position of point A is dependent on the orientation angle of the knee and the corresponding orientation angle of the knee brace 10. As such, the upper tensioning line anchor 98 is alternately termed a floating anchor and its position varies with respect to the lateral and medial upper longitudinal members 40, 46 and the lateral and medial hinges 44, 50 as well as the lateral and medial lower longitudinal members 42, 48. Conversely, the lower tensioning line anchor 106 is alternately termed a fixed anchor and its position is fixed with respect to the lateral and medial lower longitudinal members 42, 48 and the lateral and medial hinges 44, 50.

The exit point of the tensioning line 100 from the top of the upper segment 118c of the tensioning line guide is designated B. Point B is substantially on or proximal to the anterior edge of the medial upper longitudinal member 46. The lower anchor point of the lower anchored end 108 of the tensioning line 100, which is in the locking chamber of the lower tensioning line anchor 106, is designated C. Point C has a variable position relative to points A and B. The variable position of point C is likewise dependent on the orientation angle of the knee and the corresponding orientation angle of the knee brace 10.

The tensioning line path conceptually consists of two segments, a horizontal segment and a vertical segment. The horizontal segment of the tensioning line path extends between points A and B and is termed a horizontal segment because it has a substantially horizontal orientation when the knee brace 10 is mounted on the leg of a user. The horizontal component of the distance between points A and B along the horizontal segment of the tensioning line path is designated herein as the variable X. The vertical segment of the tensioning line 100 extends between points B and C and is termed a vertical segment because it has a substantially vertical orientation when the knee brace 10 is mounted on the leg of a user, particularly when the orientation angle of the knee is full extension. The vertical component of the distance between points B and C along the vertical segment is a designated herein as the variable Y.

The sum of the horizontal and vertical component distances X and Y is constant at all times during operation of the knee brace. As such, the horizontal and vertical component distances X and Y are inversely related to one another, i.e., X increases when Y decreases and X decreases when Y increases. It is likewise apparent from FIGS. 6 and 7 that the tension force on the buttress retention flap 20 and the resulting radial compression force of the buttress 18 against compression surface at the lateral side of the knee are inversely related to X and directly related to Y. Therefore, the tension force on the buttress retention flap 20 and the resulting radial compression force of the buttress 18 against the compression surface at the lateral side of the knee can be decreased by increasing X and correspondingly decreasing Y. Conversely, the tension force on the buttress retention flap 20 and the resulting radial compression force of the buttress 18 against the compression surface at the lateral side of the knee can be increased by decreasing X and correspondingly increasing Y.

As noted above, it has been found therapeutically preferable to decrease the radial compression force of the buttress 18 against the compression surface at the lateral side of the knee when the knee goes to flexion and to increase the radial compression force when the knee goes to extension. The knee brace 10 is designed to function in precisely this manner. In particular, when the knee goes to extension as shown in FIG. 6, points B and C on the knee brace 10 move further apart, thereby increasing the distance Y, which is the vertical component of the distance between points B and C. Because of the inverse relation between X and Y, points A and B necessarily simultaneously move closer together, thereby decreasing the distance X, which is the horizontal component of the distance between points A and B. As a result of the decreased horizontal component of the distance between points A and B at knee extension, which is designated $X_1$, and the increased vertical component of the distance between points B and C at knee extension, which is designated $Y_1$, the knee brace 10 desirably automatically increases the radial compression force of the buttress 18 against the compression surface at the lateral side of the knee at extension.

Figure 7:
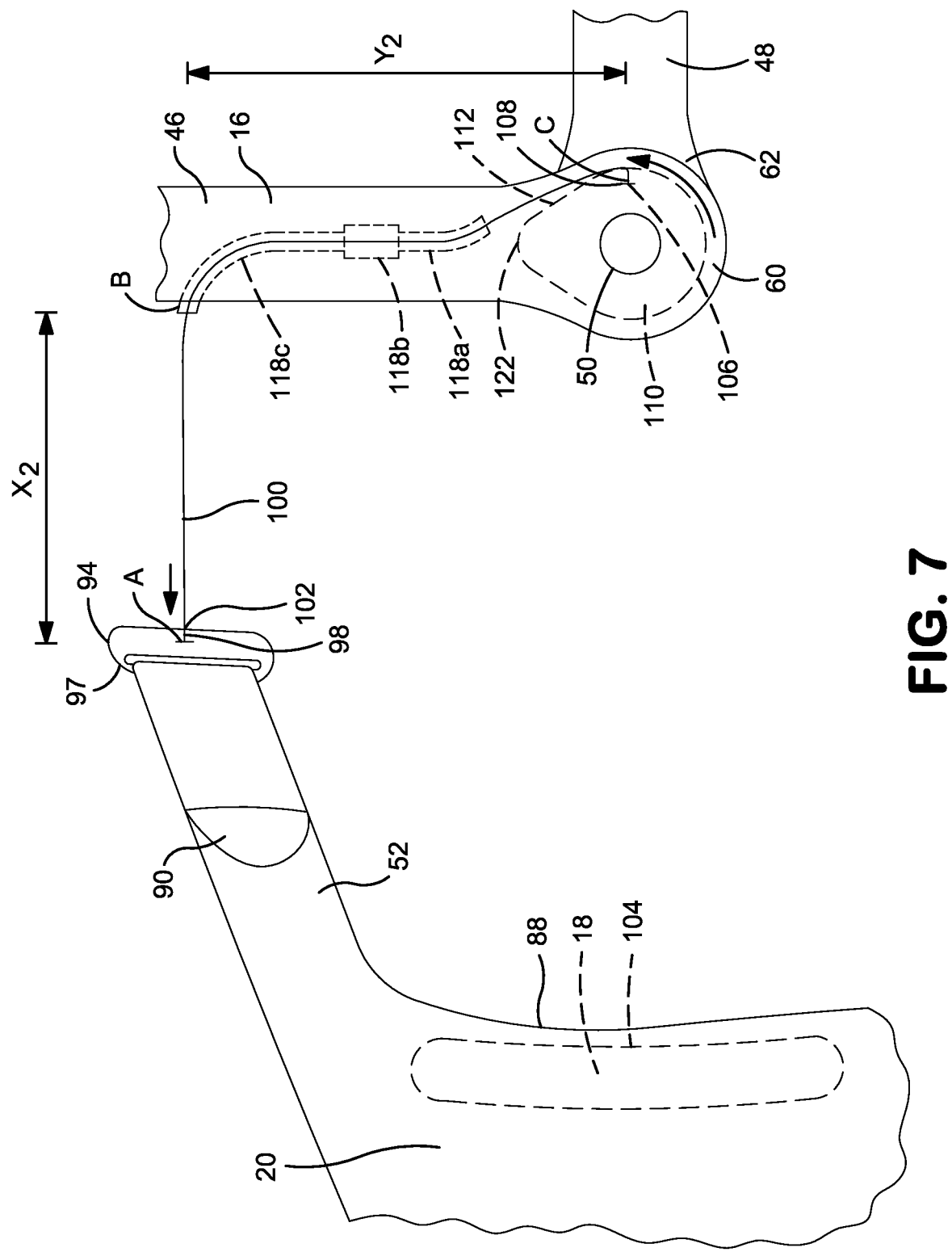
FIG. 7 is a conceptualized view from the front of a tensioning line path for the knee brace of FIG. 1 and its cooperative relation with other elements of the knee brace when the knee is in a position of flexion at 90°.

When the knee goes to flexion as shown in FIG. 7, the opposite occurs. In particular, points B and C on the knee brace 10 move closer together, thereby reducing the distance Y, while points A and B necessarily simultaneously move further apart, thereby increasing the distance X. As a result of the increased horizontal component of the distance between points A and B at knee flexion, which is designated $X_2$, and the decreased vertical component of the distance between points A and B at knee flexion, which is designated $Y_2$, the knee brace 10 automatically desirably decreases radial compression force of the buttress 18 against the compression surface at the lateral side of the knee at flexion.

Positioning the rotational tensioning line cam 110 in the tensioning line path as described herein significantly enhances the ability of the knee brace 10 to automatically self-adjust the forces it generates in response to changes in the orientation angle of the knee due to flexion or extension. It has been shown above that rotation of the medial upper and lower longitudinal members 46, 48 relative to one another about the medial hinge 50 during knee flexion or extension has the effect of shortening or lengthening the vertical component of the distance between points B and C, wherein point C is fixed to the intersecting end 62 of the medial lower longitudinal member 48 proximal to the medial hinge 50 and point B is essentially fixed to the medial lower longitudinal member 48 proximal to the opposite end thereof and more distal from the medial hinge 50.

By comparison, the tensioning line cam 110 is configured and positioned relative to the medial hinge 50 so that rotating the tensioning line cam 110 while the tensioning line 100 rests against its operating surface 112 has the advantageous effect of automatically increasing or decreasing the travel distance of the tensioning line 100 within the vertical segment of the tensioning line path while simultaneously inversely decreasing or increasing the travel distance of the tensioning line 100 within the horizontal segment of the tensioning line path in response to changes in the orientation angle of the knee due to flexion or extension respectively.

The travel length of the tensioning line in the vertical segment of the tensioning line path, which extends between points B and C, is defined herein as the actual total length the tensioning line travels within the vertical segment independent of whether the contribution to this length has a horizontal or vertical orientation. The travel length of the tensioning line in the horizontal segment of the tensioning line path, which extends between points A and B, is similarly defined as the actual total length the tensioning line travels within the horizontal segment independent of whether the contribution to this length has a horizontal or vertical orientation.

The above-referenced effect of the tensioning line cam 110 on the travel length of the tensioning line 100 is attributed to placement of an out-of-round offset point 122 on the operating surface 112 of the tensioning line cam 110. Rotation of the knee and the medial lower longitudinal member 48 of the knee brace 10 in the clockwise direction toward extension causes the tensioning line cam 110 to rotate in the clockwise direction as shown in FIG. 6. The offset point 122 is positioned on the operating surface 112 relative to the tensioning line path such that the offset point 122 moves toward the tensioning line path into underlying engagement with the tensioning line 100 when the knee and knee brace 10 approach extension. As a result, the underlying offset point 102 urges the tensioning line 100 radially outward away from the centrally positioned medial hinge 50 and increases the travel length of the tensioning line 100 in the vertical segment of the tensioning line path, thereby maximizing the loading of the radial compression force on the buttress 18. This effect is most pronounced in an angular range of the knee from about 0° (full extension) to about 30° due to the specific positioning and configuration of the offset point 122 on the operating surface 112 of the tensioning line cam 110.

Conversely, rotation of the knee and the medial lower longitudinal member 48 of the knee brace 10 in the counter-clockwise direction toward flexion causes the tensioning line cam 110 to rotate in the counter-clockwise direction as shown in FIG. 7. The offset point 122 is positioned on the operating surface 112 relative to the tensioning line path such that the offset point 122 moves away from the tensioning line path and away from underlying engagement with the tensioning line 100 when the knee and knee brace 10 move toward flexion. Instead, a more evenly rounded segment of the operating surface 112 of the tensioning line cam 110 moves into underlying engagement with the tensioning line 100 in place of the underlying offset point 122. As a result, the tensioning line 100 moves radially inward toward the centrally positioned medial hinge 50 and decreases the travel length of the tensioning line 100 in the vertical segment of the tensioning line path, thereby offloading the radial compression force from the buttress 18. This effect is most pronounced in an angular range of the knee from about 30° to about 120° (full flexion).

In sum, it is evident that the knee brace 10 advantageously automatically self-adjusts the magnitude of the therapeutically useful radial compression force applied to the knee in response to changes in the orientation angle of the knee due to flexion or extension. In particular, the knee brace 10 desirably increases the magnitude of the treatment force applied to the knee when the knee travels from flexion to full extension (see directional arrow in FIG. 6). The increased magnitude of the treatment force is directly attributable to the following two factors in this case: (1) automatically increasing the vertical component of the vertical segment of the tensioning line path while automatically decreasing the horizontal component of the horizontal segment of the tensioning line path by rotating the medial upper and lower longitudinal members 46, 48 away from one another about the medial hinge 50; and (2) automatically increasing the travel length of the tensioning line 100 within the vertical component of the tensioning line path while automatically decreasing the travel length of the tensioning line 100 within the horizontal component of the tensioning line path by rotating the offset point 122 on the operating surface 12 of the tensioning line cam 110 into underlying engagement with the tensioning line 100.

The knee brace 10 desirably decreases the magnitude of the treatment force applied to the knee when the knee travels from full extension to flexion (see directional arrow in FIG. 7). The decreased magnitude of the treatment force is directly attributable to the same two factors in this case, but in reverse: (1) automatically decreasing the vertical component of the vertical segment of the tensioning line path while automatically increasing the horizontal component of the horizontal segment of the tensioning line path by rotating the medial upper and lower longitudinal members 46, 48 toward one another about the medial hinge 50; and (2) automatically decreasing the travel length of the tensioning line 100 within the vertical component of the tensioning line path while automatically increasing the travel length of the tensioning line 100 within the horizontal component of the tensioning line path by rotating the offset point 122 on the operating surface 112 of the tensioning line cam 110 out away from underlying engagement with the tensioning line 100.

Figure 9:
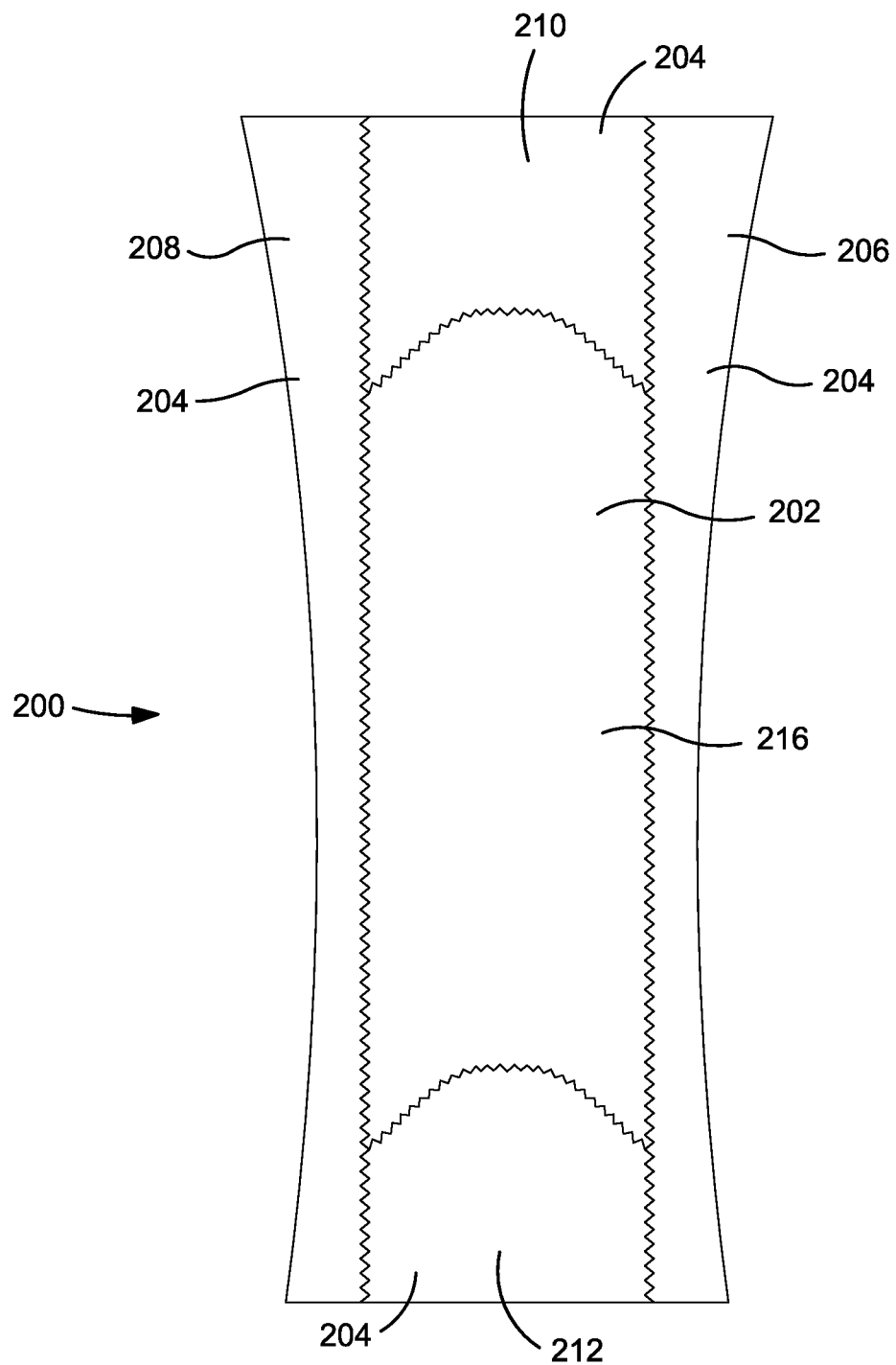
FIG. 9 is a posterior elevational view of the knee sleeve of FIG. 8.

Referring to FIGS. 8-10, a specific alternate embodiment of a knee sleeve is shown and generally designated 200. The knee sleeve 200 has specific utility in the knee brace 10 and has general utility in other framed or hybrid-type knee braces known in the art. The knee sleeve 200 also has general utility as a standalone soft knee brace. For purposes of illustration, the embodiment of the knee sleeve 200 shown in the drawings and described herein is configured to be worn on the right leg of a user. However, it is apparent to one of ordinary skill in the art from the teaching herein that the knee sleeve 200 can be readily adapted for wearing on the left leg of a user The knee sleeve 200 comprises a tube-shaped main body 202 which is similar in construction to the main body 24 of the above-described knee sleeve 12. As such, the main body 202 is a unitary structure having a continuous face which is preferably constructed from a sheet of pliant material. However, the main body 202 differs from the main body 24 insofar as the present main body 202 is provided with a plurality of overlays 204 superimposed atop its outside face.

The overlays 204 are integrally joined to the main body 202 by substantially permanent attachment or fastening means such as sewing, gluing, welding, or the like. Alternatively, the overlays 204 are integrally joined to the main body 202 by releasable attachment or fastening means, such as hook and loop fasteners, zippers, hooks, snaps, buttons or the like.

The pliant material of the main body 202 is preferably sufficiently elastically stretchable to at least apply a perceptible compression force to the leg when the main body 202 snugly encloses the leg. A material for constructing the main body 202 satisfying the above criteria is preferably selected from among fabrics, cloths, foams, meshes, elastomers and combinations thereof. A most preferred material from among this group is an elastically stretchable synthetic cloth, such as nylon or the like, which has some beneficial compression properties. Alternatively, though less preferred, the pliant material of the main body 202 can be pliant, but substantially non-stretchable.

The material of each overlay 204 is likewise pliant and preferably elastic, being selectable from the substantially same type of materials as those of the main body 202 listed above. The material of each overlay 204 may be the same or different for each respective overlay. In any case, the preferred material of the overlays 204 is generally characterized as having different compression properties than the material of the main body 202 and is most preferably a material having substantially greater compression properties than the material of the main body 202. This enables the material of the overlays 204 to apply a substantially greater therapeutic radial compression force to the underlying leg than the material of the main body 202 when the materials of the main body 202 and overlays 204 are integrated into the present knee sleeve 200 in the manner described herein.

Alternatively, the material of the overlays 204 may be substantially the same as the material of the main body 202 and have substantially the same compression properties. In this case, however, the combined compression properties of the material of the main body 202 and overlays 204 in combination, nevertheless, differ from the compression properties of each material individually, even when they are the same material, due to the cumulative effect of two compressive materials integrated together one atop the other in accordance with the construction of the knee sleeve 200 described herein. Accordingly, all sections on of the knee sleeve 200 which are occupied by overlays 204 are characterized as having different compression properties, and more particularly having substantially greater compression properties, than the main body 202 alone, which enables sections of the knee sleeve 200 occupied by the overlays 204 to apply a substantially greater therapeutic radial compression force to the underlying leg than sections of the knee sleeve 200 which are not occupied by the overlays 204, but are only occupied by the main body 202.

The sections of the knee sleeve 200 which are delineated by the overlap area of each overlay 204 atop the main body 202 are termed herein enhanced compression panels. The present knee sleeve 200 comprises an alternating pattern of enhanced compression panels interspersed with interposing sections which do not have an overlapping overlay, thereby exposing the outside faces of the main body 202. These interposing sections are termed herein reduced compression panels. The present pattern of alternating enhanced and reduced compression panels shown by way of example in FIGS. 8-10 comprises a lateral longitudinal enhanced compression panel 206 having a lateral longitudinal overlay, a medial longitudinal enhanced compression panel 208 having a medial longitudinal overlay, a posterior upper enhanced compression panel 210 having a posterior upper overlay, a posterior lower enhanced compression panel 212 having a posterior lower overlay, an anterior longitudinal reduced compression panel 214 and a posterior intermediate reduced compression panel 216.

The lateral and medial longitudinal enhanced compression panels 206, 208 and their corresponding overlays extend the entire length of the knee sleeve 200. The anterior longitudinal reduced compression panel 214 likewise extends the entire length of the knee sleeve 200. In contrast, the posterior upper and lower enhanced compression panels 210, 212 and their corresponding overlays only extend a partial length of the knee sleeve 200. The posterior intermediate reduced compression panel 216 likewise only extends a partial length of the knee sleeve 200.

The knee sleeve 200 is positioned on the leg of a user in substantially the same manner as described above with respect to the knee sleeve 12 so that the knee sleeve 200 advantageously aligns its specific pattern of alternating enhanced and reduced compression panels with the underlying knee. In particular, the knee sleeve 200 is positioned on the leg such that the anterior longitudinal reduced compression panel 214 overlies the patella and the anterior segments of the leg immediately above and below the knee. The posterior intermediate reduced compression panel 216 overlies the back of the knee termed the popliteal. The posterior upper and lower enhanced compression panels 210, 212 overlie the posterior segments of the leg immediately above and below the popliteal respectively. The lateral and medial longitudinal enhanced compression panels 206, 208 overlie the lateral and medial sides the knee and the lateral and medial segments of the leg immediately above and below the knee respectively.

It is believed that the above-described pattern of alternating enhanced and reduced compression panels confers a number of therapeutic benefits on a user of the knee sleeve 200. In particular, the pattern of alternating enhanced and reduced compression panels improves dynamic proprioception at the position on the body of a user where the knee sleeve is worn, i.e., the knee and immediately adjacent upper and lower legs. Improved proprioception generally has a desirable therapeutic effect on a user rehabilitating and/or stabilizing a knee which exhibits symptoms of patellar tracking disorders. The pattern of alternating enhanced and reduced compression panels also enables the knee sleeve 200 to emulate and/or enhance the mechanical venous return function of live tissue in the knee region by having alternating zones of higher and lower compression side by side against the body. The alternating zones of higher and lower compression alternately tension and relax the adjoining tissue which is a primary mechanism for venous return. As a result, the knee sleeve 200 beneficially improves circulation and reduces or prevents swelling of tissue in the knee region due to edema or trauma.

The present pattern of alternating enhanced and reduced compression panels also confers a decidedly practical benefit on a user of the knee sleeve 200. In particular, the knee sleeve 200 recognizes that it is generally desirable to reduce the compression force a knee brace applies to the patella as well as the compression force a knee brace applies to the popliteal to increase user comfort and to minimize interference of the knee brace with full range of motion activity of the knee.

Notwithstanding the above, it is understood that the knee sleeve of the present invention is not limited to any one particular pattern of alternating enhanced and reduced compression panels, such as the particular pattern shown and described herein, but contemplates knee sleeves having other patterns of alternating enhanced and reduced compression panels. Thus, it is within the scope of the present invention to reverse the relative positions of the main body 202 and the overlays 204 without substantially altering the properties and performance of the knee sleeve 200. In accordance with this modification, the overlays 204 are overlapped by the main body 202 rather than vice versa as recited above. However, such a knee sleeve retains the same pattern of alternating enhanced and reduced compression panels as when the overlays 204 overlap the main body 202.

It is further within the scope of the present invention to augment the main body 202 with supplemental compression components such as flaps, straps, strap retainers, releasable fasteners and the like. For example, the main body can be augmented by the attachment of a sleeve tensioning flap and/or associated straps thereto. In particular, the present knee sleeve 200 can be substituted for the main body 24 in the knee sleeve 12 described above, augmented with the identical supplemental components of the knee sleeve 12, i.e., the sleeve tensioning flap 26, buttress 18, buttress retention flap 20, upper and lower buttress straps 52, 54, etc., and incorporated into the knee brace 10 in place of the knee sleeve 12.

An alternate embodiment of a knee sleeve (not shown) can be constructed in a patchwork manner entirely from discrete patches of material having differing compression properties without an underlying unitary main body. In other words, the patchwork knee sleeve of the present embodiment omits an underlying continuous unitary main body and its tubular structure consists essentially in its entirety of a pattern of integrally inter-connected patches which have been substantially permanently joined together by substantially permanent or releasable attachment means such as those described above.

It is readily apparent that a patchwork knee sleeve can be constructed as a pattern of patches which has a substantially identical outward appearance to the pattern of alternating enhanced and reduced compression panels of the knee sleeve 200 and which has substantially identical performance characteristics to the knee sleeve 200. This is achieved simply by selecting material for the patches which has compression properties matching up with the alternating enhanced and reduced compression panels of the knee sleeve 200.

It further apparent from the above that the present invention may alternately be characterized as not just a knee sleeve, but in a more general sense as an orthopedic sleeve which has alternating zones of compression properties interspersed across the tubular expanse of the orthopedic sleeve that afford the orthopedic sleeve desirable functional performance characteristics and confer therapeutic benefits on a user. The orthopedic sleeve is adaptable as described herein to the knee and is alternately adaptable to other regions of the body and, in particular, to other joints of the body, e.g., ankle, wrist, elbow, etc., and such other adaptations of the sleeve are within the scope of the present invention.

While the forgoing preferred embodiments of the invention have been described and shown, it is understood that alternatives and modifications, such as those suggested and others, may be made thereto and fall within the scope of the present invention.

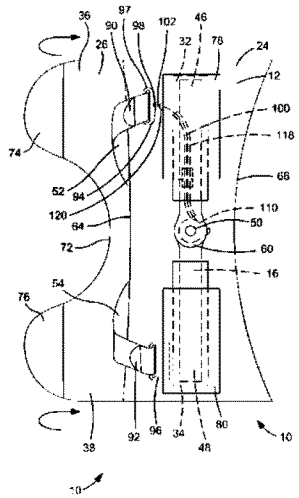

We claim:

1. A variable tensioning assembly for an orthopedic knee brace comprising:

a longitudinal support assembly including a first longitudinal member having a proximal end and a distal end, a second longitudinal member having a proximal end and a distal end and a pivot rotatably connecting said proximal ends of said first and second longitudinal members to one another such that said first and second longitudinal members are rotatable relative to one another about said pivot and said pivot positions said first and second longitudinal members at a rotation angle between 90° and 0°, inclusively, wherein said first and second longitudinal members are aligned perpendicular relative to one another at a full flexion position corresponding to a 90° rotation angle and said first and second longitudinal members are aligned collinear relative to one another at a full extension position corresponding to a 0° rotation angle, and wherein said pivot is adapted to be positioned adjacent to a knee joint in horizontal alignment therewith when said orthopedic knee brace is in an operative position on a leg of a user;

a tensioning line flexible and having a variable line tension, a first anchored end and a second anchored end;

a tensioning line path between said first anchored end and said second anchored end; and a rotatable cam fixably attached at said pivot to said proximal end of said first longitudinal member, such that said rotatable cam maintains a constant fixed stationary position at all times relative to said first longitudinal member, but is rotationally displaceable about said pivot relative to said second longitudinal member in identical correspondence with said first longitudinal member when said first longitudinal member is rotationally displaced about said pivot relative to said second longitudinal member, wherein said rotatable cam has an arcuate operating surface positioned in said tensioning line path and said arcuate operating surface has an out of round offset point adapted to engage said tensioning line when said first and second longitudinal members rotate away from one another toward said full extension position and said rotation angle decreases below an automatic tension transition point and adapted to disengage said tensioning line when said first and second longitudinal members rotate toward one another toward said full flexion position and said rotation angle increases above said automatic tension transition point.

2. The variable tensioning assembly of claim 1 further comprising a knee sleeve including a main body formed from a pliant material with a tube-like structure adapted to be positioned over the knee joint, wherein said longitudinal support assembly and said main body engage one another and said main body is adapted to maintain said pivot adjacent to the knee joint in horizontal alignment therewith.

3. The variable tensioning assembly of claim 2, wherein said main body has an anterior portion, a medial portion, a posterior portion and a lateral portion, said longitudinal support assembly is positioned at said lateral or medial portion of said main body, said knee sleeve further includes a buttress retention flap positioned in horizontal alignment with said pivot and adapted to be positioned adjacent to the knee joint in horizontal alignment therewith when said orthopedic knee brace is in said operative position, said buttress retention flap has a first side and a second side opposite said first side, said first side is attached to said lateral or medial portion of said main body opposite said longitudinal support assembly, said second side extends from said lateral or medial portion of said main body opposite said longitudinal support assembly, said second anchored end of said tensioning line is connected to said second side of said buttress retention flap and said first anchored end of said tensioning line is fixably attached to said rotatable cam.

4. The variable tensioning assembly of claim 3 further comprising a buttress strap retainer anchored to said second anchored end of said tensioning line, wherein said buttress retention flap has a buttress strap extending from said second side of said buttress retention flap and attachable to said buttress strap retainer, said buttress strap and said buttress strap retainer thereby enabling connection of said second anchored end of said tensioning line to said second side of said buttress retention flap.

5. The variable tensioning assembly of claim 3, wherein said longitudinal support assembly is a medial longitudinal support assembly engaging said medial portion of said main body, said first longitudinal member is a medial lower longitudinal member, said second longitudinal member is a medial upper longitudinal member, and said pivot is a medial hinge, said variable tensioning assembly further comprising a lateral longitudinal support assembly opposite said medial longitudinal support assembly and engaging said lateral portion of said main body, said lateral longitudinal support assembly including a lateral lower longitudinal member, a lateral upper longitudinal member, and a lateral hinge rotatably connecting said lower and upper longitudinal members of said lateral longitudinal support assembly to one another.

6. The variable tensioning assembly of claim 3 further comprising a knee buttress laying beneath said buttress retention flap such that said buttress retention flap is adapted to apply said variable line tension to said knee buttress, wherein said knee buttress is formed from a less pliant material than said buttress retention flap, is positioned in horizontal alignment with said pivot and is adapted to be positioned adjacent to the knee joint in horizontal alignment therewith when said orthopedic knee brace is in said operative position.

7. The variable tensioning assembly of claim 1, wherein said tensioning line path is segmented into a vertical segment and a horizontal segment and said tensioning line has a fixed length but, a variable travel distance within said vertical segment and a variable travel distance within said horizontal segment, wherein rotation of said rotatable cam varies said travel distance in said vertical segment and said travel distance in said horizontal segment, and wherein rotation of said rotatable cam into selective engagement of said offset point with said tensioning line increases said travel distance in said vertical segment, decreases said travel distance in said horizontal segment and correspondingly increases said variable line tension while rotation of said rotatable cam into selective disengagement of said offset point with said tensioning line decreases said travel distance in said vertical segment, increases said travel distance in said horizontal segment and correspondingly decreases said variable line tension thereby adjusting said variable line tension.

8. The variable tensioning assembly of claim 1, wherein said rotation angle is between about 30° and 35° at said automatic tension transition point.

9. The variable tensioning assembly of claim 1, wherein said rotatable cam is adapted to automatically adjust said variable tensioning assembly from a higher tension state to a lower tension state when said rotation angle increases past said automatic tension transition point, thereby decreasing said variable line tension.

10. The variable tensioning assembly of claim 1, wherein said rotatable cam is adapted to automatically adjust said variable tensioning assembly from a lower tension state to a higher tension state when said rotation angle decreases past said automatic tension transition point, thereby increasing said variable line tension.

11. The variable tensioning assembly of claim 1, wherein said tensioning line path includes a tensioning line guide attached to said second longitudinal member and providing a walled passageway for said tensioning line therethrough extending along a longitudinal axis of said second longitudinal member.

12. The variable tensioning assembly of claim 1, wherein said longitudinal support assembly is a first longitudinal support assembly, said first longitudinal member is a lower longitudinal member, said second longitudinal member is an upper longitudinal member, and said pivot is a first hinge, said variable tensioning assembly further comprising a second longitudinal support assembly opposite said first longitudinal support assembly including a lower longitudinal member, an upper longitudinal member, and a second hinge rotatably connecting said lower and upper longitudinal members of said second longitudinal support assembly to one another.

13. The variable tensioning assembly of claim 1, wherein said variable tensioning assembly is capable of being positioned in a longitudinally vertical orientation when said first and second longitudinal members are aligned collinear relative to one another at said full extension position and when said variable tensioning assembly is positioned in said longitudinally vertical orientation, said first anchored end of said tensioning line is fixably attached to said rotatable cam, said tensioning line path extends therefrom in a vertical direction upwardly away from said pivot along a longitudinal axis of said second longitudinal member toward said distal end of said second longitudinal member distally from and vertically above said pivot and redirects therefrom in a horizontal direction laterally away from said second longitudinal member to said second anchored end of said tensioning line.

14. A variable tensioning assembly for an orthopedic knee brace comprising:
a longitudinal support assembly including a lower longitudinal member having a proximal end and a distal end, an upper longitudinal member having a proximal end and a distal end and a pivot rotatably connecting said proximal ends of said lower and upper longitudinal members to one another such that said lower and upper longitudinal members are rotatable relative to one another about said pivot and said pivot positions said lower and upper longitudinal members at a rotation angle between 90° and 0°, inclusively, wherein said lower and upper longitudinal members are aligned perpendicular relative to one another at a full flexion position corresponding to a 90° rotation angle and said lower and upper longitudinal members are aligned collinear relative to one another at a full extension position corresponding to a 0° rotation angle, and wherein said pivot is adapted to be positioned adjacent to a knee joint in horizontal alignment therewith when said orthopedic knee brace is in an operative position on a leg of a user;
a tensioning line having a variable line tension, a first anchored end and a second anchored end;
a tensioning line path between said first anchored end and said second anchored end; and
a rotatable cam fixably attached at said pivot to said proximal end of said lower longitudinal member, such that said rotatable cam maintains a constant fixed stationary position at all times relative to said lower longitudinal member, but is rotationally displaceable about said pivot relative to said upper longitudinal member in identical correspondence with said lower longitudinal member when said lower longitudinal member is rotationally displaced about said pivot relative to said upper longitudinal member, wherein said rotatable cam has an arcuate operating surface positioned in said tensioning line path and said arcuate operating surface has an out of round offset point adapted to engage said tensioning line when said lower and upper longitudinal members rotate away from one another toward said full extension position and said rotation angle decreases below an automatic tension transition point and adapted to disengage said tensioning line when said lower and upper longitudinal members rotate toward one another toward said full flexion position and said rotation angle increases above said automatic tension transition point.

15. The variable tensioning assembly of claim 14, wherein said rotation angle is between about 30° and 35° at said automatic tension transition point.

16. The variable tensioning assembly of claim 14, wherein said rotatable cam is adapted to automatically adjust said variable tensioning assembly from a lower tension state to a higher tension state when said rotation angle decreases past said automatic tension transition point, thereby increasing said variable line tension.

17. A variable tensioning assembly for an orthopedic knee brace comprising:
a longitudinal support assembly including a first longitudinal member having a proximal end and a distal end, a second longitudinal member having a proximal end and a distal end and a pivot rotatably connecting said proximal ends of said first and second longitudinal members to one another such that said first and second longitudinal members are rotatable relative to one another about said pivot and said pivot positions said first and second longitudinal members at a rotation angle between 90° and 0°, inclusively, wherein said first and second longitudinal members are aligned perpendicular relative to one another at a full flexion position corresponding to a 90° rotation angle and said first and second longitudinal members are aligned collinear relative to one another at a full extension position corresponding to a 0° rotation angle, and wherein said pivot is adapted to be positioned adjacent to a knee joint in horizontal alignment therewith when said orthopedic knee brace is in an operative position on a leg of a user;
a knee sleeve including a main body formed from a pliant material with a tube-like structure adapted to be positioned over the knee joint, wherein said longitudinal support assembly and said main body engage one another and said main body is adapted to maintain said pivot adjacent to the knee joint in horizontal alignment therewith, wherein said main body has an anterior portion, a medial portion, a posterior portion and a lateral portion, wherein said longitudinal support assembly is positioned at said medial portion of said main body opposite said lateral portion;
said knee sleeve further including a buttress retention flap positioned in horizontal alignment with said pivot and adapted to be positioned adjacent to the knee joint in horizontal alignment therewith when said orthopedic knee brace is in said operative position, wherein said buttress retention flap has a first side and a second side opposite said first side, said first side is attached to said lateral portion of said main body and said second side extends from said lateral portion of said main body;

a tensioning line having a variable line tension, a first anchored end and a second anchored end, wherein said second anchored end is connected to said second side of said buttress retention flap;

a tensioning line path between said first anchored end and said second anchored end; and a rotatable cam fixably attached to said first anchored end of said tensioning line and at said pivot to said proximal end of said first longitudinal member, such that said rotatable cam maintains a constant fixed stationary position at all times relative to said first longitudinal member, but is rotationally displaceable about said pivot relative to said second longitudinal member in identical correspondence with said first longitudinal member when said first longitudinal member is rotationally displaced about said pivot relative to said second longitudinal member, wherein said rotatable cam has an arcuate operating surface positioned in said tensioning line path and said arcuate operating surface has an out of round offset point adapted to engage said tensioning line when said first and second longitudinal members rotate away from one another toward said full extension position and said rotation angle decreases below an automatic tension transition point and adapted to disengage said tensioning line when said first and second longitudinal members rotate toward one another toward said full flexion position and said rotation angle increases above said automatic tension transition point.

18. The variable tensioning assembly of claim 17, wherein said rotatable cam is adapted to automatically adjust said variable tensioning assembly from a lower tension state to a higher tension state when said rotation angle decreases past said automatic tension transition point, thereby increasing said variable line tension.

19. The variable tensioning assembly of claim 17, wherein said variable tensioning assembly is capable of being positioned in a longitudinally vertical orientation when said first and second longitudinal members are aligned collinear relative to one another at said full extension position and when said variable tensioning assembly is positioned in said longitudinally vertical orientation, said first anchored end of said tensioning line is fixably attached to said rotatable cam, said tensioning line path extends therefrom in a vertical direction upwardly away from said pivot along a longitudinal axis of said second longitudinal member toward said distal end of said second longitudinal member distally from and vertically above said pivot and said knee buttress and redirects therefrom in a horizontal direction laterally away from said second longitudinal member to said second anchored end of said tensioning line.

20. The variable tensioning assembly of claim 17 further comprising a knee buttress laying beneath said buttress retention flap such that said buttress retention flap is adapted to apply said variable line tension to said knee buttress, wherein said knee buttress is formed from a less pliant material than said buttress retention flap, is positioned in horizontal alignment with said pivot and is adapted to be positioned adjacent to the knee joint in horizontal alignment therewith when said orthopedic knee brace is in said operative position.

* * * * *

UNITED STATES PATENT AND TRADEMARK OFFICE
CERTIFICATE OF CORRECTION

PATENT NO. : 10,617,550 B2
APPLICATION NO. : 14/738774
DATED : April 14, 2020
INVENTOR(S) : Shane C. Fedon and Andrew M. Blecher It is certified that error appears in the above-identified patent and that said Letters Patent is hereby corrected as shown below:

On the Title Page

Delete the title page and substitute therefore with the attached title page consisting of the corrected illustrative figure.

In the Drawings

Please replace FIGS. 1-10 with FIGS. 1-10 as shown on the attached pages.

Signed and Sealed this
Twenty-third Day of June, 2020

Andrei Iancu
*Director of the United States Patent and Trademark Office*

(12) United States Patent
Fedon et al.

(10) Patent No.: US 10,617,550 B2
(45) Date of Patent: Apr. 14, 2020

(54) KNEE BRACE HAVING A VARIABLE TENSIONING OFFSET CAM

(71) Applicant: Breg, Inc., Carlsbad, CA (US)

(72) Inventors: Shane C. Fedon, Encinitas, CA (US); Andrew M. Blecher, Encino, CA (US)

(73) Assignee: Breg, Inc., Carlsbad, CA (US)

(*) Notice: Subject to any disclaimer, the term of this patent is extended or adjusted under 35 U.S.C. 154(b) by 722 days.

(21) Appl. No.: 14/738,774

(22) Filed: Jun. 12, 2015

(65) Prior Publication Data
US 2015/0374531 A1 Dec. 31, 2015

Related U.S. Application Data

(60) Provisional application No. 62/018,575, filed on Jun. 28, 2014.

(51) Int. Cl.
*A61F 5/01* (2006.01)
*A61F 5/02* (2006.01)

(52) U.S. Cl.
CPC .......... *A61F 5/0125* (2013.01); *A61F 5/0102* (2013.01); *A61F 5/0193* (2013.01); *A61F 5/02* (2013.01); *A61F 2005/0155* (2013.01)

(58) Field of Classification Search
CPC .... A61F 5/0102; A61F 5/0123; A61F 5/0125; A61F 5/013; A61F 5/058; A61F 5/0585; A61F 5/05841; A61F 5/05825; A61F 5/05858; A61F 2005/0134; A61F 2005/0137; A61F 2005/0144; A61F 2005/0146; A61F 2005/0148; A61F 2005/0151; A61F 2005/0153; A61F 2005/0155; A61F 2005/0165; A61F 2005/0169; A61F 2005/0179; A61F 2005/0181; A61F 5/01; A61F 5/0104; A61F 5/0106; A61F 5/0109; A61F 5/0118; A61F 2005/0132; A61F 2005/0167

See application file for complete search history.

(56) References Cited

U.S. PATENT DOCUMENTS

| | | | |
|---|---|---|---|
| 4,296,744 A | 10/1981 | Palumbo |
| 4,370,977 A | 2/1983 | Mauldin |
| 4,370,978 A | 2/1983 | Palumbo |
| 4,397,308 A | 8/1983 | Hepburn |
| 4,423,720 A | 1/1984 | Meier |
| 4,445,505 A | 5/1984 | Labour |
| 4,489,718 A | 12/1984 | Martin |
| 4,508,111 A | 4/1985 | Hepburn |

(Continued)

FOREIGN PATENT DOCUMENTS

| | | |
|---|---|---|
| CA | 2831507 | 4/2015 |

*Primary Examiner* — Victoria J Hicks
*Assistant Examiner* — Rachel A Berezik
(74) *Attorney, Agent, or Firm* — Rodney F. Brown

(57) ABSTRACT

A knee brace to stabilize the patella has a main body positionable over the knee, a hinged longitudinal support assembly, a buttress, a buttress retention flap overlaying the buttress, a cam positioned proximal to the support assembly and a tensioning line. The buttress is positioned against the side of the knee opposite the support assembly and applies a variable compression force to the knee. The tensioning line engages the cam and operatively connects it to the buttress via the buttress retention flap to automatically vary the compression force applied to the knee in response to rotation of the support assembly.

20 Claims, 10 Drawing Sheets